United States Patent
Kumar et al.

(10) Patent No.: US 8,924,165 B2
(45) Date of Patent: Dec. 30, 2014

(54) MEASURING SYSTEM HAVING A MEASURING TRANSDUCER OF VIBRATION-TYPE

(75) Inventors: Vivek Kumar, Muttenz (CH); Martin Anklin, Dornach (CH)

(73) Assignee: Endress + Hauser Flowtec AG, Reinach (CH)

( * ) Notice: Subject to any disclaimer, the term of this patent is extended or adjusted under 35 U.S.C. 154(b) by 477 days.

(21) Appl. No.: 12/981,239

(22) Filed: Dec. 29, 2010

(65) Prior Publication Data

US 2011/0161017 A1   Jun. 30, 2011

Related U.S. Application Data

(60) Provisional application No. 61/291,648, filed on Dec. 31, 2009.

(30) Foreign Application Priority Data

Dec. 31, 2009 (DE) .......................... 10 2009 060 915
Jan. 11, 2010 (DE) .......................... 10 2010 000 759

(51) Int. Cl.
G01F 7/00  (2006.01)
G01F 1/84  (2006.01)
G01N 11/02  (2006.01)

(52) U.S. Cl.
CPC ............ *G01F 1/8477* (2013.01); *G01F 1/8413* (2013.01); *G01F 1/8418* (2013.01); *G01F 1/8427* (2013.01); *G01F 1/8431* (2013.01); *G01F 1/8436* (2013.01); *G01N 11/02* (2013.01)
USPC .............................................. 702/47; 702/50

(58) Field of Classification Search
CPC ...................................................... G01N 11/02
USPC ................................................... 702/47, 45, 50
See application file for complete search history.

(56) References Cited

U.S. PATENT DOCUMENTS 5,473,949 A     12/1995  Cage
6,513,393 B1 *  2/2003   Eckert et al. ............. 73/861.357

(Continued)

FOREIGN PATENT DOCUMENTS

CN           1303474 A       7/2001
DE      10 2005 014 058 A1   6/2006

(Continued)

OTHER PUBLICATIONS

International Search Report, Jul. 1, 2011.

(Continued)

*Primary Examiner* — Eliseo Ramos Feliciano
*Assistant Examiner* — Eman Alkafawi
(74) *Attorney, Agent, or Firm* — Bacon & Thomas, PLLC

(57) ABSTRACT

The measuring system has a measuring transducer which produces primary signals transmitter electronics for activating the measuring transducer and for evaluating primary signals. The measuring transducer includes at least one measuring tube; at least one electro-mechanical, oscillation exciter, a first oscillation sensor. The transmitter electronics, in turn, delivers at least one driver signal for the oscillation exciter for effecting vibrations of the at least one measuring tube and generates, by means of the first primary signal and by means of the second primary signal, as well as with application of a Reynolds number, measured value representing a Reynolds number, Re, for medium flowing in the measuring transducer, a pressure difference, measured value, which represents a pressure difference occurring between two predetermined reference points in the flowing medium.

48 Claims, 12 Drawing Sheets

(56) References Cited

U.S. PATENT DOCUMENTS

| | | |
|---|---|---|
| 7,406,878 B2 | 8/2008 | Rieder |
| 7,665,369 B2 * | 2/2010 | Bitto et al. ............... 73/861.355 |
| 2002/0065614 A1 | 5/2002 | Bugarin |
| 2006/0107759 A1 | 5/2006 | Kolahi |
| 2006/0173639 A1 | 8/2006 | Carpenter |
| 2006/0181583 A1 * | 8/2006 | Usuda ............................. 347/85 |
| 2009/0013798 A1 * | 1/2009 | Hocker ...................... 73/861.03 |
| 2009/0103989 A1 * | 4/2009 | Relin et al. ...................... 406/12 |
| 2010/0043566 A1 * | 2/2010 | Hoecker ................... 73/861.24 |
| 2010/0094569 A1 * | 4/2010 | Gysling ........................ 702/47 |
| 2010/0242623 A1 * | 9/2010 | Bitto et al. ............... 73/861.356 |
| 2011/0161018 A1 * | 6/2011 | Kumar et al. ................... 702/48 |
| 2011/0259123 A1 * | 10/2011 | Bitto et al. ............... 73/861.357 |

FOREIGN PATENT DOCUMENTS

| | | |
|---|---|---|
| DE | 10 2006 044 505 A1 | 4/2007 |
| EP | 1 659 3777 A1 | 5/2006 |
| WO | WO 00/36379 | 6/2000 |
| WO | WO 2009 134268 A1 | 11/2009 |

OTHER PUBLICATIONS

English Translation of the IPR, Dec. 22, 2010.
German Search Report.

* cited by examiner

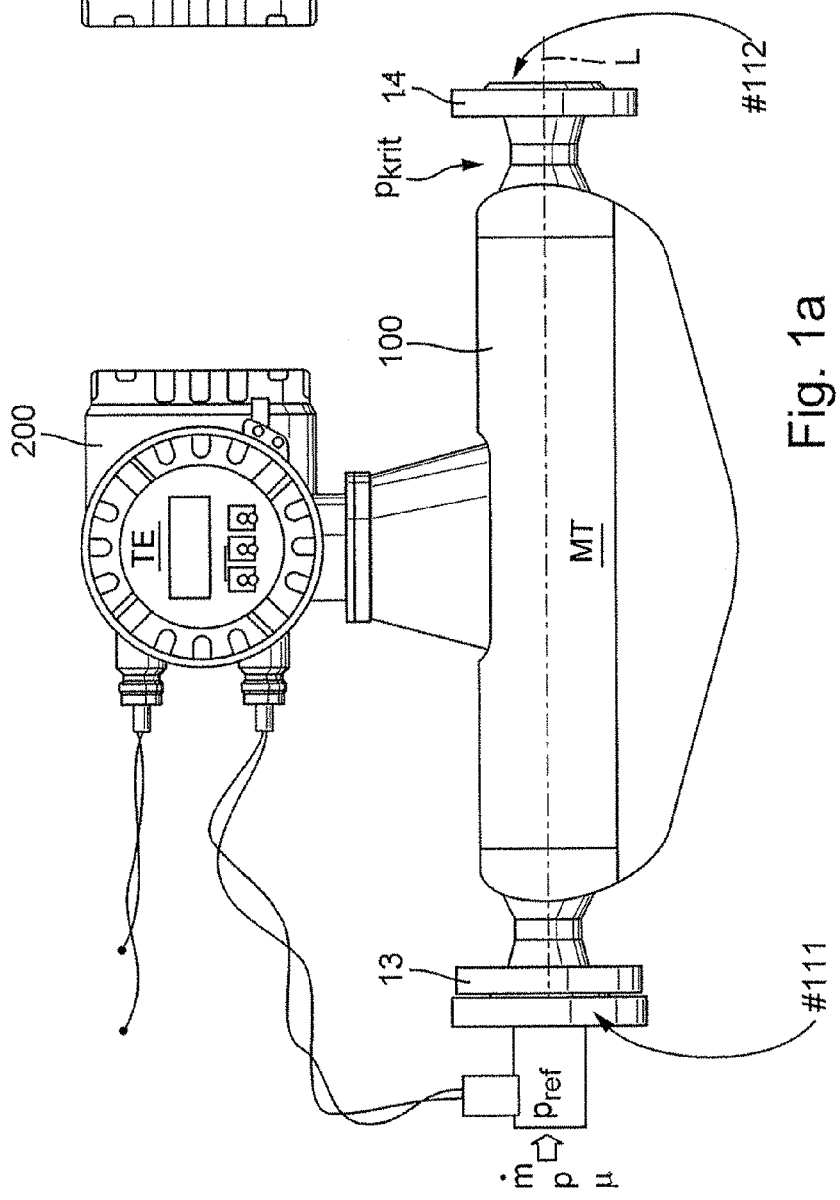
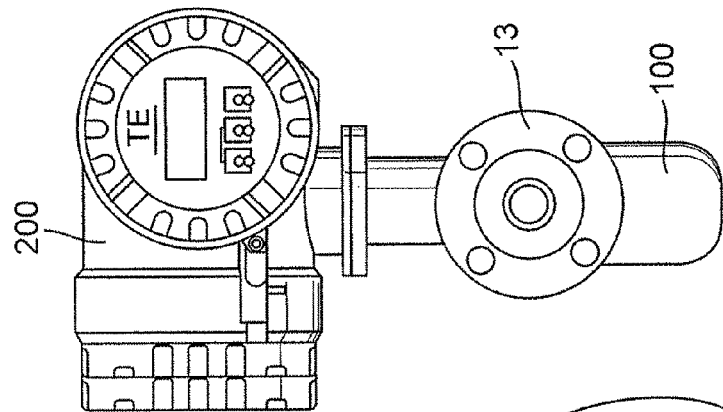
Fig. 1a
Fig. 1b

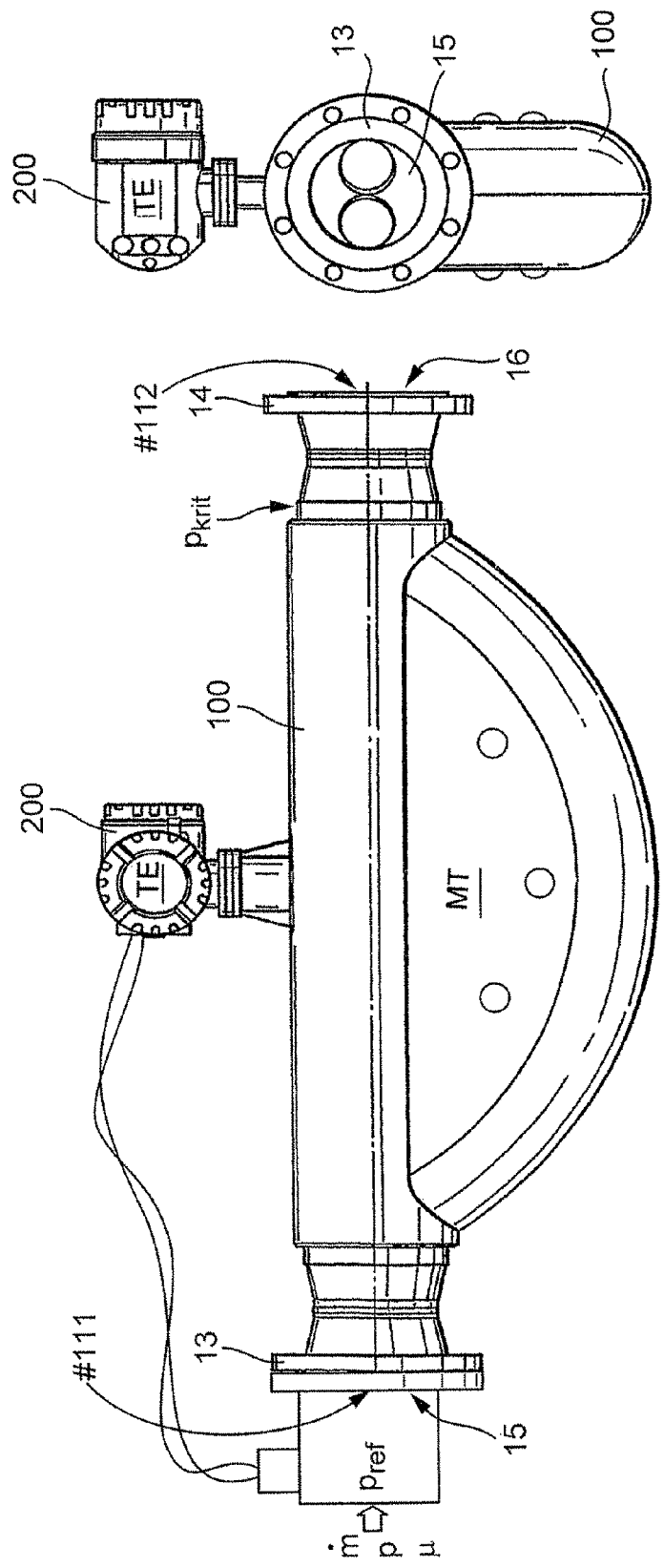

MEASURING SYSTEM HAVING A MEASURING TRANSDUCER OF VIBRATION-TYPE

CROSS-REFERENCE TO RELATED APPLICATION

This application is a Nonprovisional which claims the benefit of U.S. Provisional Application No. 61/291,648 filed on Dec. 31, 2009.

FIELD OF THE INVENTION

The invention relates to a measuring system for flowable, especially fluid, media, especially a measuring system embodied as a compact, measuring device and/or as a Coriolis mass flow measuring device, wherein the measuring system comprises: A measuring transducer of vibration-type, through which medium flows during operation at least at times and and which generates primary signals influenced by at least one measured variable, especially a mass flow, a density, a viscosity, etc., characterizing the flowing medium; as well as a transmitter electronics electrically coupled with the measuring transducer and processing into measured values primary signals delivered by the measuring transducer.

BACKGROUND OF THE INVENTION

In industrial measurements technology, especially also in connection with the control and monitoring of automated manufacturing processes, for ascertaining characteristic measured variables of media, for example, liquids and/or gases, flowing in a process line, for example, a pipeline, often such measuring systems are used, which, by means of a measuring transducer of vibration-type and a transmitter electronics connected thereto and most often accommodated in a separate, electronics housing, induce reaction forces in the flowing medium, for example, Coriolis forces, and produce, repetitively derived from these, measurement values correspondingly representing the at least one measured variable, for example, a mass flow rate, a density, a viscosity or some other process parameter. Such measuring systems—often formed by means of an In-line measuring device in compact construction with integrated measuring transducer, such as, for instance, a Coriolis mass flow meter,—are long since known and have proven themselves in industrial use. Examples of such measuring systems having a measuring transducer of vibration-type or also individual components thereof, are described e.g. in EP-A 317 340, JP-A 8-136311, JP-A 9-015015, US-A 200710119264, US-A 2007/0119265, US-A 2007/0151370, US-A 2007/0151371, US-A 2007/0186685, US-A 2008/0034893, US-A 200810141789, U.S. Pat. Nos. 4,680,974, 4,738,144, 4,777,833, 4,801,897, 4,823,614, 4,879,911, 5,009,109, 5,024,104, 5,050,439, 5,291,792, 5,359,881, 5,398,554, 5,476,013, 5,531,126, 5,602,345, 5,691,485, 5,734,112, 5,796,010, 5,796,011, 5,796,012, 5,804,741, 5,861,561, 5,869,770, 5,945,609, 5,979,246, 6,047,457, 6,092,429, 6,073,495, 6,311,136, 6,223,605, 6,330,832, 6,397,685, 6,513,393, 6,557,422, 6,651,513, 6,666,098, 6,691,583, 6,840,109, 6,868,740, 6,883,387, 7,017,424, 7,040,179, 7,073,396, 7,077,014, 7,080,564, 7,134,348, 7,216,550, 7,299,699, 7,305,892, 7,360,451, 7,392,709, 7,406,878, WO-A 00/14 485, WO-A 01/02 816, WO-A 2004/072588, WO-A 2008/013545, WO-A 2008/077574, WO-A 95/29386, WO-A 95/16897 or WO-A 99 40 394. Each of the therein illustrated measuring transducers comprises at least one, essentially straight, or curved, measuring tube accommodated in a measuring transducer housing and conveying, or guiding, the, in given cases, also extremely rapidly, or extremely slowly, flowing, medium. In operation of the measuring system, the at least one measuring tube is caused to vibrate for the purpose of generating oscillation forms influenced by the medium flowing through the measuring tube.

In the case of measuring transducers having two measuring tubes, these are most often integrated into the process line via a flow divider extending on the inlet side between the measuring tubes and an inlet-side connecting flange as well a via a flow divider extending on the outlet side between the measuring tubes and an outlet-side connecting flange. In the case of measuring transducers having a single measuring tube, the latter communicates with the process line most often via an essentially straight connecting tube piece opening on the inlet side, as well as via an essentially straight connecting tube piece opening on the outlet side. Additionally, each of the illustrated measuring transducers having a single measuring tube comprises, in each case, at least one one-piece or multipart, for example, tube-, box- or plate-shaped, counteroscillator, which is coupled to the measuring tube on the inlet side for forming a first coupling zone and which is coupled to the measuring tube on the outlet side for forming a second coupling zone, and which, during operation, essentially rests or oscillates opposite-equally to the measuring tube, thus with equal frequency and opposite phase. The inner part of the measuring transducer formed by means of measuring tube and counteroscillator is most often held, especially in a manner enabling oscillations of the inner part relative to the measuring tube, in a protective measuring transducer housing alone by means of the two connecting tube pieces, via which the measuring tube communicates during operation with the process line. In the case of the measuring transducers, for example, as illustrated in U.S. Pat. Nos. 5,291,792, 5,796, 010, 5,945,609, 7,077,014, US-A 2007/0119264, WO-A 01 02 816 or also WO-A 99 40 394, having a single, essentially straight, measuring tube, the latter and the counteroscillator are, as in the case of conventional measuring transducers quite usual, oriented essentially coaxially relative to one another. In the case of usually marketed measuring transducers of the aforementioned type, most often also the counteroscillator is essentially tubular and embodied as an essentially straight, hollow cylinder, which is so arranged in the measuring transducer, that the measuring tube is at least partially jacketed by the counteroscillator. Most often used as materials for such counteroscillators, especially also in the case of application of titanium, tantalum or zirconium for the measuring tube, are comparatively cost effective steel types, such as, for instance, structural steel or free-machining steel.

Selected as excited oscillation form—the so-called wanted mode—in the case of measuring transducers having curved, e.g. U, V- or Ω-like formed, measuring tubes is usually that eigenoscillation form, in the case of which the measuring tube moves in a pendulum-like manner at least partially in a lowest natural resonance frequency about an imaginary longitudinal axis of the measuring transducer, like a cantilever clamped on one end, whereby Coriolis forces are induced in the through flowing medium dependent on the mass flow. These forces, in turn, lead to the fact that superimposed on the excited oscillations of the wanted mode, in the case of curved measuring tubes, thus pendulum-like, cantilever oscillations, are thereto equal-frequency, bending oscillations according to at least one, likewise natural, second oscillation form, the so-called Coriolis mode. In the case of measuring transducers with curved measuring tube, these cantilever oscillations in the Coriolis mode caused by Coriolis forces usually correspond to that eigenoscillation form, in the case of which the measuring tube also executes rotary oscillations about an imaginary vertical axis directed perpendicular to the longitudinal axis. In the case of measuring transducers with straight measuring tube, in contrast, for the purpose of producing of mass flow dependent Coriolis forces, often such a wanted mode is selected, in the case of which the measuring tube executes, at least partially, bending oscillations essentially in a single imaginary plane of oscillation, such that the oscillations in the Coriolis mode are bending oscillations of equal oscillation frequency coplanar with the wanted mode oscillations. Due to the superpositioning of wanted- and Coriolis modes, the oscillations of the vibrating measuring tube registered by means of the sensor arrangement on the inlet side and on the outlet side have a measurable phase difference also dependent on the mass flow. Usually, the measuring tubes of such measuring transducers, applied e.g. in Coriolis mass flow meters, are excited during operation to an instantaneous natural resonance frequency of the oscillation form selected for the wanted mode, especially with oscillation amplitude controlled to be constant. Since this resonance frequency is dependent, especially, also on the instantaneous density of the medium, supplementally also the density of flowing media can be measured by means of market-usual Coriolis mass flow meters, in addition to the mass flow. Additionally, it is also possible, as, for example, shown in U.S. Pat. Nos. 6,651, 513 or 7,080,564, directly to measure, by means of measuring transducers of vibration-type, the viscosity of the through flowing medium, for example, based on an exciter energy or excitation power required for maintaining the oscillations, and/or based on a damping of oscillations (especially those in the aforementioned wanted mode) of the at least one measuring tube resulting from a dissipation of oscillatory energy. Moreover, also other measured variables derived from the aforementioned primary measured values of mass flow rate, density and viscosity can be ascertained, such as, for instance, the Reynolds number; compare U.S. Pat. No. 6,513,393.

For exciting oscillations of the at least one measuring tube, measuring transducers of vibration-type have, additionally, an exciter mechanism driven during operation by an electrical driver signal, e.g. a controlled electrical current, generated and correspondingly conditioned by the mentioned driver electronics. The exciter mechanism excites the measuring tube to bending oscillations in the wanted mode by means of at least one electro-mechanical, especially electro-dynamic, oscillation exciter acting practically directly on the measuring tube and flowed through during operation by an electrical current. Furthermore, such measuring transducers comprise a sensor arrangement having oscillation sensors, especially electro-dynamic oscillation sensors, for the at least pointwise registering of inlet-side and outlet-side oscillations of the at least one measuring tube, especially those in the Coriolis mode, and for producing electrical sensor signals influenced by the process parameter to be registered, such as, for instance, the mass flow or the density, and serving as primary signals of the measuring transducer. As, for example, described in U.S. Pat. No. 7,216,550, in the case of measuring transducers of the type being discussed, in given cases, also the oscillation exciter can at least at times be used as oscillation sensor and/or an oscillation sensor at least at times can be used as oscillation exciter. The exciter mechanism of measuring transducers of the type being discussed includes, usually, at least one electrodynamic oscillation exciter and/or an oscillation exciter acting differentially on the at least one measuring tube and the, in given cases, present counteroscillator or the, in given cases, present, other measuring tube, while the sensor arrangement comprises an inlet-side, most often likewise electrodynamic, oscillation sensor as well as at least one outlet-side oscillation sensor constructed essentially equally thereto. Such electrodynamic and/or differential oscillation exciters of usually marketed measuring transducers of vibration-type are formed by means of a magnet coil, through which an electrical current flows, at least at times. In the case of measuring transducers having a measuring tube and a thereto coupled counteroscillator, most often the magnet coil is affixed to the latter. Such oscillation exciters further include a rather elongated, especially rod-shaped, permanent magnet interacting with the at least one magnet coil, especially plunging into it, and serving as armature and affixed correspondingly to the measuring tube to be moved. The permanent magnet and the magnet coil serving as exciter coil are, in such case, usually so oriented, that they extend essentially coaxially relative to one another. Additionally, in the case of conventional measuring transducers, the exciter mechanism is usually embodied in such a manner and so placed in the measuring transducer, that it acts essentially centrally on the at least one measuring tube. In such case, the oscillation exciter (and, insofar, the exciter mechanism) is, such as, for example, also shown in the case of the measuring transducers proposed in U.S. Pat. Nos. 5,796,010, 6,840,109, 7,077,014 or 7,017,424, most often affixed at least pointwise along an imaginary central, peripheral line of the measuring tube outwardly thereon. Alternatively to an exciter mechanism formed by means of oscillation exciters acting rather centrally and directly on the measuring tube, as, among other things, provided in U.S. Pat. No. 6,557,422, 6,092,429 or 4,823,614, for example, also exciter mechanisms formed by means of two oscillation exciters affixed not in the center of the measuring tube, but, instead, rather at the inlet and outlet sides, respectively, thereof can be used, or, as, among other things, provided in U.S. Pat. Nos. 6,223,605 or 5,531,126, for example, also exciter mechanisms formed by means of an oscillation exciter acting between the, in given cases, present counteroscillator and the measuring transducer housing can be used. In the case of most market-usual measuring transducers of vibration-type, the oscillation sensors of the sensor arrangement are, as already indicated, at least, insofar as they work according to the same principle of action, embodied essentially of equal construction as the at least one oscillation exciter. Accordingly, also the oscillation sensors of such a sensor arrangement are most often formed, in each case, by means of at least one magnet coil—usually affixed to the, in given cases, present counteroscillator—, at least at times passed through by a variable magnetic field and, associated therewith, at least at times supplied with an induced measurement voltage, as well as by means of a permanently magnetic armature, which delivers the magnetic field. The armature is affixed to the measuring tube and interacts with the at least one coil. Each of the aforementioned coils is additionally connected by means of at least one pair of electrical connecting lines with the mentioned transmitter electronics of the in-line measuring device. The connecting lines are led most often on as short as possible paths from the coils via the counteroscillator to the measuring transducer housing.

As, among other things, discussed in the initially mentioned U.S. Pat. Nos. 7,406,878, 7,305,892, 7,134,348, 6,513, 393, 5,861,561, 5,359,881 or. WO-A 2004/072588, a further parameter quite relevant for the operation of the measuring system as such and/or for the operation of the plant, in which the measuring system is installed, can be a pressure loss in the flow—, for example, a pressure loss caused by the measuring transducer and, insofar, by the measuring system. Pressure loss in the flow is important, especially, also for the case, in which the medium has two- or more phases, for instance, a liquid gas mixture, and/or in which one must contend with, or necessarily prevent, during operation, undesired cavitation as a result a subceeding, or falling beneath, of a minimum static pressure in the flowing medium. In the case of the measuring systems illustrated in U.S. Pat. Nos. 5,359,881 or 7,406,878, a pressure drop across the measuring transducer during operation is, for example, ascertained by the features that, at a first pressure measuring point in the inlet region of the measuring transducer, or directly upstream therefrom, a first static pressure in the flowing medium is registered by means of a first pressure sensor, and, at a second pressure measuring point in the outlet region of the measuring transducer, or directly downstream therefrom, a second static pressure in the flowing medium is registered by means of an additional, second pressure sensor, and, by means of hydraulic pressure measuring mechanism and/or by means of the respective transmitter electronics, these are repetitively converted into a corresponding pressure difference, measured value. In U.S. Pat. Nos. 7,305,892, or 7,134,348, there is additionally described a method executable by means of a measuring transducer of vibration-type for measuring a pressure difference, in the case of which, on the basis of an oscillatory response of the at least one measuring tube to a multimodal oscillation excitation, as well as on the basis of physical-mathematical models furnished in the transmitter electronics for the dynamics of the measuring system (formed here as a Coriolis, mass flow measuring device), a pressure, or pressure drop, in the medium flowing through the measuring transducer is ascertained.

A disadvantage of the solutions known from the state of the art for pressure measurement, especially also for pressure difference measuring by means of measuring transducer of vibration-type, is, however, to be seen in the fact that either correspondingly modified exciter mechanisms and/or correspondingly modified driver electronics need to be used, or, however, additional pressure sensors provided. Associated therewith, both the design complexity of the measuring system as well as also the experimental effort in the calibrating of such measuring systems increase in extreme measure, since the foundational physical mathematical models for the pressure—, or the pressure difference, measuring, for the purpose of achieving a high accuracy of measurement, are very complex, and have, associated therewith, a large number of coefficients, which need to be supplementally calibrated, in given cases, also in the course of a wet-calibration performed first on-site at the installed measuring system.

SUMMARY OF THE INVENTION

An object is of the invention, consequently, is to improve measuring systems formed by means of measuring transducers of vibration-type toward the goal that, therewith, a measuring of a pressure difference in the through flowing medium is enabled, which is, at least for purposes of detection, or alarming, of undesirably high pressure drops in the flowing medium, sufficiently exact, and, in given cases, also highly precise, in the sense of producing validated, measured values; this should be accomplished, especially, also with application of the measurements technology proven in such measuring systems, such as, for instance, established oscillation sensors and/or actuation technology, or also proven technologies and architectures of established transmitter electronics.

For achieving the object, the invention resides in a measuring system, for example, a compact, measuring device and/or Coriolis, mass flow measuring device, for, for example, media flowing in pipelines, which measuring system comprises: A measuring transducer of vibration-type, through which, during operation, a medium, for example, a gas and/or a liquid, a paste or a powder or other flowable material, flows, and which produces primary signals corresponding to parameters of the flowing medium, for example, a mass flow rate, a density and/or a viscosity; as well as a transmitter electronics (TE) electrically coupled with the measuring transducer for activating the measuring transducer and for evaluating primary signals delivered by the measuring transducer. The measuring transducer includes: At least one measuring tube for conveying flowing medium; at least one electro-mechanical, for example, electrodynamic, oscillation exciter for exciting and/or maintaining vibrations of the at least one measuring tube, for example, bending oscillations of the at least one measuring tube executed about an imaginary oscillation axis imaginarily connecting an inlet-side, first measuring tube end of the measuring tube and an outlet-side, second measuring tube end of the measuring tube and having a natural resonance frequency of the measuring transducer; a, for example, electrodynamic, first oscillation sensor for registering, for example, inlet-side vibrations of at least the at least one measuring tube and for producing a first primary signal of the measuring transducer representing, for example, inlet-side vibrations at least of the at least one measuring tube; and a, for example, electrodynamic, second oscillation sensor for registering, for example, outlet-side vibrations at least of the at least one measuring tube and for producing a second primary signal of the measuring transducer representing, for example, outlet-side vibrations at least of the at least one measuring tube. The transmitter electronics, in turn, delivers at least one driver signal for the oscillation exciter for effecting vibrations, for example, bending oscillations, of the at least one measuring tube, and generates, by means of the first primary signal and by means of the second primary signal, as well as with application of a Reynolds number, measured value, for example, held internally in a volatile data memory of the transmitter electronics and/or produced during operation by means of the driver signal and/or by means of at least one of the primary signals, and representing a Reynolds number, Re, for medium flowing in the measuring transducer, a pressure difference, measured value, which represents a pressure difference occurring between two predetermined reference points in the flowing medium located, for example, within the measuring transducer, for example, in such a manner, that a first of the two reference points is located on the inlet side and a second of the two reference points is located on the outlet side in the measuring transducer.

Moreover, the invention resides in a method for measuring a pressure difference arising within a flowing medium, which method comprises steps as follows:
  permitting the medium to flow through at least one measuring tube;
  producing a Reynolds number, measured value representing a Reynolds number, Re, for the flowing medium, as well as
  applying the Reynolds number, measured value for producing a pressure difference, measured value, which represents a pressure difference occurring between two reference points in the flowing medium, for example, reference points located within the measuring transducer.

According to a first embodiment of the measuring system of the invention, it is additionally provided, that the transmitter electronics generates the Reynolds number-measured value by means of the driver signal.

According to a second embodiment of the measuring system of the invention, it is additionally provided, that the transmitter electronics generates the Reynolds number-measured value by means of the first primary signal and/or by means of the second primary signal.

According to a third embodiment of the measuring system of the invention, it is additionally provided, that the transmitter electronics generates the pressure difference, measured value with application of a viscosity, measured value representing a viscosity, η, of medium flowing in the measuring transducer, for example, a viscosity, measured value internally held in a volatile data memory of the transmitter electronics and/or a viscosity, measured value produced during operation by means of the driver signal and/or by means of at least one of the primary signals. Developing this embodiment of the invention further, it is additionally provided, that the transmitter electronics generates the viscosity, measured value by means of the driver signal and/or that the transmitter electronics generates the viscosity, measured value with application of the first primary signal and/or the second primary signal.

According to a fourth embodiment of the measuring system of the invention, it is additionally provided, that the transmitter electronics, for ascertaining the pressure difference, measured value by means of the first primary signal and by means of the second primary signal, generates a phase difference, measured value, which represents a phase difference, $\Delta\phi_1$, existing between the first primary signal and the second primary signal, for example, a phase difference, $\Delta\phi_1$, dependent on a mass flow rate, $\dot{m}$, of medium flowing in the measuring transducer.

According to a fifth embodiment of the measuring system of the invention, it is additionally provided, that the transmitter electronics, for ascertaining the pressure difference, measured value and/or for producing a density, measured value representing a density, ρ, of medium flowing in the measuring transducer on the basis of at least one of the primary signals and/or on the basis of the at least one driver signal, generates a frequency, measured value, which represents an oscillation frequency, $f_{exc}$, of vibrations of the at least one measuring tube, for example, of bending oscillations of the at least one measuring tube executed about an imaginary oscillation axis imaginarily connecting an inlet-side, first measuring tube end of the measuring tube and an outlet-side, second measuring tube end of the measuring tube and having a natural resonance frequency of the measuring transducer.

According to a sixth embodiment of the measuring system of the invention, it is additionally provided, that the transmitter electronics, for ascertaining the pressure difference, measured value by means of the first primary signal and by means of the second primary signal, generates a mass flow, measured value, which represents a mass flow rate, $\dot{m}$, of medium flowing in the measuring transducer, According to a seventh embodiment of the measuring system of the invention, it is additionally provided, that the transmitter electronics generates the Reynolds number, measured value with application of a mass flow, measured value representing a mass flow rate, $\dot{m}$, of medium flowing in the measuring transducer.

According to an eighth embodiment of the measuring system of the invention, it is additionally provided, that the transmitter electronics generates the Reynolds number, measured value with application of a viscosity, measured value representing a viscosity, η, of medium flowing in the measuring transducer.

According to a ninth embodiment of the measuring system of the invention, it is additionally provided, that the transmitter electronics generates the Reynolds number, measured value with application both of a mass flow, measured value representing a mass flow rate, $\dot{m}$, of medium flowing in the measuring transducer as well as also a viscosity, measured value representing a viscosity, η, of medium flowing in the measuring transducer.

According to a tenth embodiment of the measuring system of the invention, it is additionally provided, that the transmitter electronics generates the pressure difference, measured value with application of a density, measured value representing a density, ρ, of medium flowing in the measuring transducer, for example, a density, measured value internally held in a volatile data memory of the transmitter electronics and/or produced during operation by means of the driver signal and/or by means of at least one of the primary signals.

According to an eleventh embodiment of the measuring system of the invention, it is additionally provided, that the transmitter electronics, for ascertaining the pressure difference, measured value by means of the first primary signal and by means of the second primary signal, generates a flow energy, measured value, which represents a kinetic energy, $\rho U^2$, of medium flowing in the measuring transducer dependent on a density, ρ, and a flow velocity, U, of medium flowing in the measuring transducer.

According to a twelfth embodiment of the measuring system of the invention, it is additionally provided, that the transmitter electronics, for ascertaining the pressure difference, measured value, generates a pressure drop coefficient, which represents a pressure drop across the measuring transducer dependent on the instantaneous Reynolds number, Re, of the flowing medium, referenced to an instantaneous kinetic energy of the medium flowing in the measuring transducer.

According to a thirteenth embodiment of the measuring system of the invention, it is additionally provided, that the transmitter electronics, with application of the pressure difference, measured value and on the basis of a first pressure, measured value internally held, for example, in a volatile data memory of the transmitter electronics and representing, for example, a first pressure reigning in the flowing medium upstream of an outlet end of the measuring transducer and/or downstream of an inlet end of the measuring transducer, measured, for example, by means of a pressure sensor communicating with the transmitter electronics and/or ascertained by means of the first and second primary signals of the measuring transducer, generates a second pressure, measured value, which represents, for example, a minimum static pressure, $p_{crit}$, within the flowing medium and/or a static pressure, $p_{crit}$, classified as critical for the measuring system. Developing this embodiment of the invention further, it is additionally provided, that the transmitter electronics, with application of the second pressure, measured value, generates an alarm, which signals, for example, visually and/or acoustically perceivably, a subceeding, or falling beneath, of an earlier defined, minimum allowable static pressure in the medium; and/or that the transmitter electronics, with application of the second pressure, measured value, generates an alarm, which signals, for example, visually and/or acoustically perceivably, a, for example, impending, occurrence of cavitation in the medium.

According to a fourteenth embodiment of the measuring system of the invention, such comprises, for producing a pressure, measured value representing a static pressure reigning in the flowing medium, further a pressure sensor serving for registering a static pressure reigning, for example, upstream of an inlet end of the measuring transducer or downstream of an outlet end of the measuring transducer, in a pipeline conveying the medium, and for communicating with the transmitter electronics during operation.

According to a fifteenth embodiment of the measuring system of the invention, it is additionally provided, that the transmitter electronics, with application of the pressure difference, measured value, generates an alarm, which signals, for example, visually and/or acoustically perceivably, an exceeding of an earlier defined, maximum allowable drop of a static pressure in the medium flowing through the measuring transducer; and/or that the transmitter electronics, with application of the pressure difference, measured value, generates an alarm, which signals, for example, visually and/or acoustically perceivably, a too high pressure drop in the medium, as caused by the measuring transducer.

According to a sixteenth embodiment of the invention, it is additionally provided, that the measuring transducer further includes a measuring transducer housing having an inlet-side, first housing end, especially one having a connecting flange for a line segment supplying medium to the measuring transducer, and an outlet-side, second housing end, especially one having a connecting flange for a line segment removing medium from the measuring transducer. Developing this embodiment of the invention further, it is additionally provided, that the inlet-side, first housing end of the measuring transducer housing is formed by means of an inlet-side, first flow divider having two, mutually spaced flow openings and the outlet-side, second housing end of the measuring transducer housing is formed by means of an outlet-side, second flow divider, having two, mutually spaced flow openings, and that the measuring transducer has two, mutually parallel measuring tubes for conveying flowing medium, of which a first measuring tube opens with an inlet-side, first measuring tube end into a first flow opening of the first flow divider and with an outlet-side, second measuring tube end into a first flow opening of the second flow divider, and a second measuring tube opens with an inlet-side, first measuring tube end into a second flow opening of the first flow divider and with an outlet-side, second measuring tube end into a second flow opening of the second flow divider.

According to a first embodiment of the method of the invention, such further comprises steps of exciting the at least one measuring tube to execute vibrations, for example, bending oscillations about an imaginary oscillation axis imaginarily connecting an inlet-side, first measuring tube end of the measuring tube and an outlet-side, second measuring tube end of the measuring tube; as well as producing a first primary signal representing inlet-side vibrations at least of the at least one measuring tube, as well as a second primary signal representing outlet-side vibrations at least of the at least one measuring tube. Developing this embodiment of the invention further, the method further comprises a step of applying the first primary signal and/or the second primary signal for producing the Reynolds number, measured value, especially also for producing a density, measured value representing a density of the flowing medium and/or for producing a mass flow, measured value representing a mass flow rate of the flowing medium.

A basic idea of the invention is to apply a small number of measurement values established for measuring flowing media, such as mass flow rate, density, viscosity and/or Reynolds number, which are typically available in any event in measuring systems of the type being discussed, especially also are internally ascertained, and/or on the basis of some few operating parameters typically internally generated by means of the transmitter electronics of such measuring systems, such as a phase difference between the primary signals representing in- and outlet-side oscillations of the at least one measuring tube, their signal frequency and/or -amplitude, or the parameters in any event typically derived therefrom, to ascertain, as another measured variable of interest, a pressure difference. The invention is based, in such case, also on the surprising recognition, that even alone on the basis of the aforementioned operating parameters, or the therefrom derived, in measuring systems of the type being discussed typically in any event ascertained, measured values as well as some few earlier specially—, for instance, in the course of an in any event desired, wet-calibration—to be determined, measuring system specific constants, pressure differences in the medium flowing through the measuring transducer can be ascertained with an accuracy of measurement sufficiently good also for purposes of issuing alarms indicating critical operating states, such as, for instance, cavitation in the flowing medium; this can also be accomplished over a very broad Reynolds number range, thus both for laminar as well as also for turbulent flow. An advantage of the invention is, in such case, especially, that, for implementing the pressure difference measuring of the invention, both operationally proven, conventional measuring transducers as well as also operationally proven, conventional transmitter electronics, adapted, of course, as regards the software implemented for the evaluation of the invention, can be used.

The invention as well as other advantageous embodiments thereof will now be explained in greater detail on the basis of examples of embodiments presented in the figures of the drawing. Equal parts are provided in all figures with equal reference characters; when perspicuity requires or it otherwise appears sensible, already mentioned reference characters are omitted in subsequent figures. Other advantageous embodiments or further developments, especially also combinations of first only individually explained aspects of the invention, will become evident additionally from the figures of the drawing, as well as also on the basis of the dependent claims per se.

BRIEF DESCRIPTION OF THE DRAWINGS

The figures of the drawing show as follows:

FIGS. 1a, b in different side views, a variant of a measuring system embodied as a compact, measuring device for media flowing in pipelines;

FIGS. 2a, b in different side views, another variant of a measuring system embodied as a compact, measuring device for media flowing in pipelines;

DETAILED DESCRIPTION OF EXEMPLARY EMBODIMENTS

Figure 3:
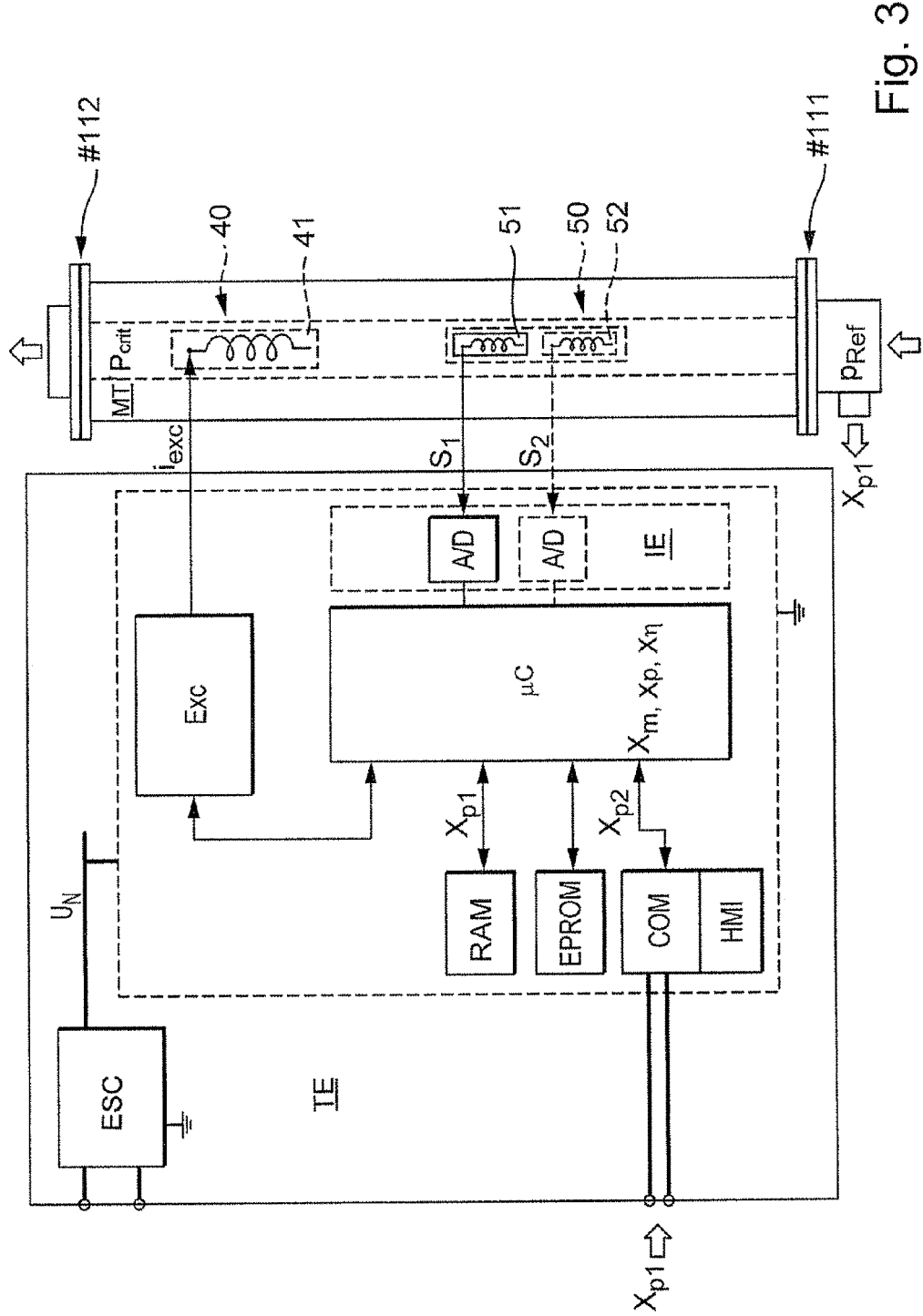
FIG. 3 schematically in the manner of a block diagram, a transmitter electronics having connected thereto a measuring transducer of vibration-type, especially a transmitter electronics suitable for a measuring system according to FIGS. 1a, 1b, 2a, 2b.

While the invention is susceptible to various modifications and alternative forms, exemplary embodiments thereof have been shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention as defined by the intended claims.

FIG. 1a, 1b, or 2a, 2b show, in each case, a variant of a measuring system suitable for flowable, especially fluid, media and insertable in a process line, for instance, a pipeline of an industrial plant, for example, a measuring system formed by means of a Coriolis, mass flow measuring device, a density measuring device, a viscosity measuring device or the like, which serves, especially, for measuring and/or monitoring a pressure difference of a medium flowing in the process line, on occasion, also, of course, for measuring and/or monitoring at least one additional physical, measured variable of the medium, such as, for instance, a mass flow rate, a density, a viscosity or the like. The measuring system, implemented here by means of an in-line measuring device in compact construction, comprises therefor a measuring transducer MT of vibration-type connected to the process line via an inlet end #111 as well as an outlet end #112, through which measuring transducer there flows during operation correspondingly the medium to be measured, such as, for instance, a low viscosity liquid and/or a high viscosity paste and/or a gas, and which is connected to a transmitter electronics TE of the measuring system, especially a transmitter electronics supplied during operation with electrical energy from the exterior via connecting cable and/or internally by means of an energy storer. The transmitter electronics includes, as shown in FIG. 3 schematically in the manner of a block diagram, a driver circuit Exc serving for activating the measuring transducer MT as well as a measuring- and evaluating circuit µC of the measuring system for processing primary signals of the measuring transducer MT. The measuring- and evaluating circuit µC is formed, for example, by means of a microcomputer and/or communicates during operation with the driver circuit Exc. During operation, the measuring- and evaluating circuit µC delivers measured values representing at least one measured variable, such as e.g. instantaneous, or totalled, mass flow. The driver circuit Exc and the evaluating circuit µC as well as other electronics components of the transmitter electronics serving the operation of the measuring system, such as, for instance, internal energy supply circuits ESC for providing internal supply voltages $U_N$ and/or communication circuits COM serving for connection to a superordinated measurement data processing system and/or to a fieldbus, are additionally accommodated in a corresponding electronics housing 200, especially a housing formed impact- and/or also explosion resistantly and/or hermetically sealedly. For visualizing measuring system internally produced measured values and/or, in given cases, measuring system internally generated status reports, such as, for instance, an error report or an alarm, on-site, the measuring system can, furthermore, have a display- and operating element HMI communicating at least at times with the transmitter electronics. The display- and operating element can include, for instance, an LCD-, OLED- or TFT-display placed in the electronics housing behind a window correspondingly provided therein, as well as a corresponding input keypad and/or a touchscreen. In advantageous manner, the transmitter electronics TE, especially a programmable and/or remotely parameterable, transmitter electronics, can additionally be so designed, that it can exchange during operation of the in-line measuring device with a thereto superordinated electronic data processing system, for example, a programmable logic controller (PLC), a personal computer and/or a work station, via a data transmission system, for example, a fieldbus system and/or wirelessly per radio, measuring- and/or other operating data, such as, for instance, current measured values or tuning- and/or diagnostic values serving for control of the in-line measuring device. In such case, the transmitter electronics TE can have, for example, an internal energy supply circuit ESC, which is fed during operation via the aforementioned fieldbus system by an energy supply provided externally in the data processing system. In an embodiment of the invention, the transmitter electronics is additionally so embodied, that it is electrically connectable by means of a two-wire-connection 2L, for example, configured as a 4-20 mA-current loop, with the external electronic data processing system and can be supplied thereby with electrical energy. Measured values can, as well, be transmitted thereover to the data processing system. For the case, in which the measuring system is to be coupled to a fieldbus—or other communication system, the transmitter electronics TE can have a corresponding communication interface COM for data communication according to one of the relevant industry standards. The electrical connecting of the measuring transducer to the transmitter electronics can occur by means of corresponding connecting lines, which are led out from the electronics housing 200, for example, via cable feed-through, and extend at least sectionally within the measuring transducer housing. The connecting lines can, in such case, be embodied, at least partially as electrical wires, at least sectionally encased in an electrical insulation, e.g. in the form of "twisted-pair" lines, flat ribbon cables and/or coaxial cables. Alternatively thereto or in supplementation thereof, the connecting lines can at least sectionally also be formed by means of conductive traces of an, especially flexible, in given cases, lacquered, circuit board; compare, for this, also the initially mentioned U.S. Pat. Nos. 6,711,958 or 5,349,872.

FIGS. 4 and 5, or 6 and 7, show schematically, for additional explanation of the invention, first, and second examples of embodiments for a measuring transducer MT of vibration-type suited for implementing the measuring system. The measuring transducer MT serves generally for producing in a through flowing medium, for instance, a gas and/or a liquid, mechanical reaction forces, e.g. mass flow dependent, Coriolis forces, density dependent, inertial forces and/or viscosity dependent, frictional forces, which react measurably, especially registerably by sensor, on the measuring transducer. Derived from these reaction forces, e.g., a mass flow m, a density ρ and/or a viscosity η of the medium can be measured. Any measuring transducer comprises therefor an inner part arranged in a measuring transducer housing 100 for actually effecting the physical-electrical transducing of the at least one parameter to be measured. Additionally to accommodating the inner part, the measuring transducer housing 100 can additionally also serve to hold the electronics housing 200 of the in-line measuring device with therein accommodated driver- and evaluating circuits.

Figure 4:
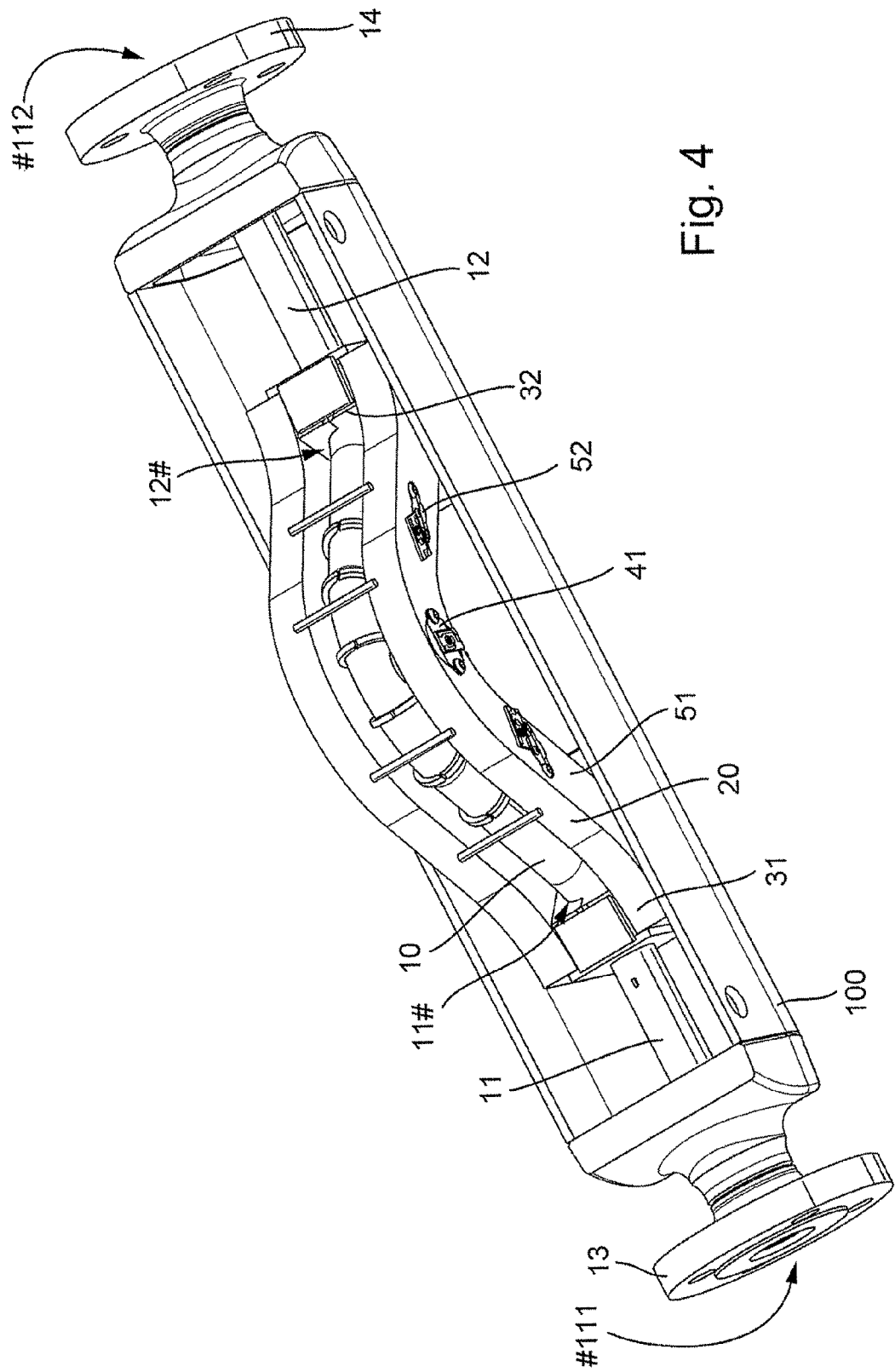
FIGS. 4, 5 in partially sectioned, or perspective, views, a variant of a measuring transducer of vibration-type, especially a measuring transducer suitable for a measuring system according to FIGS. 1a, 1b.
Figure 5:
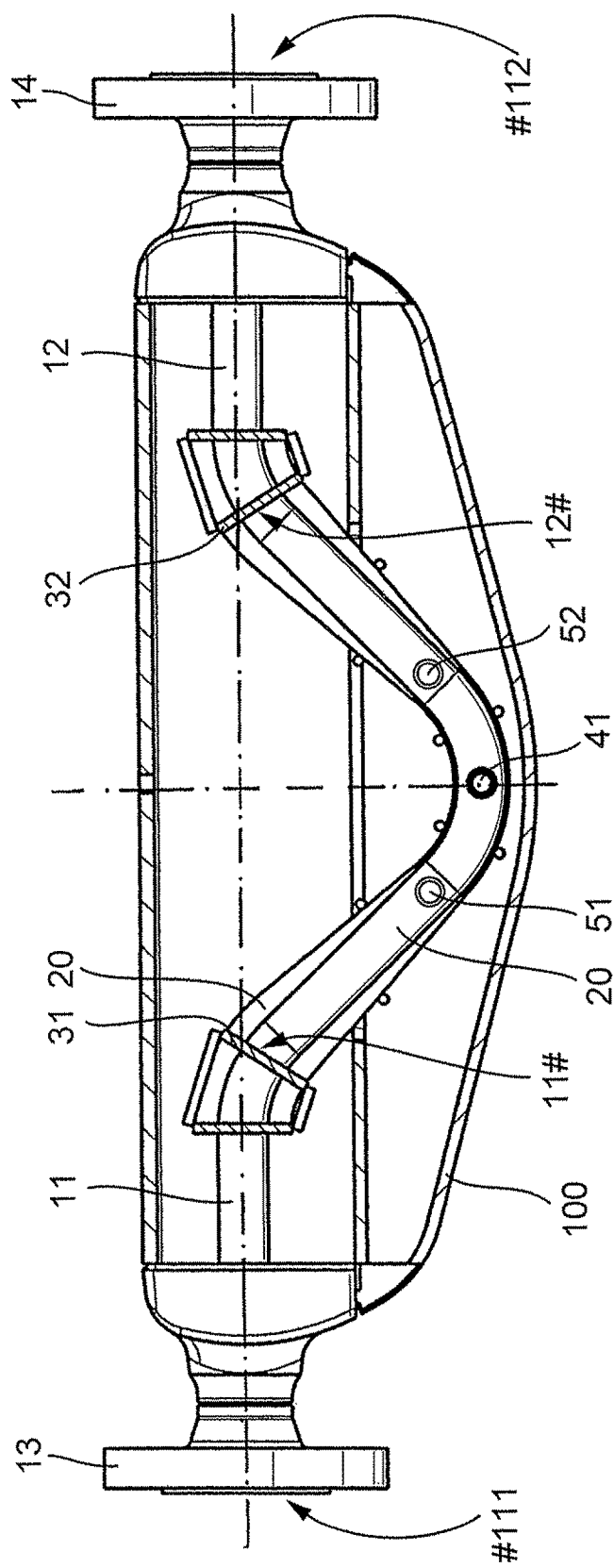
Figure 6:
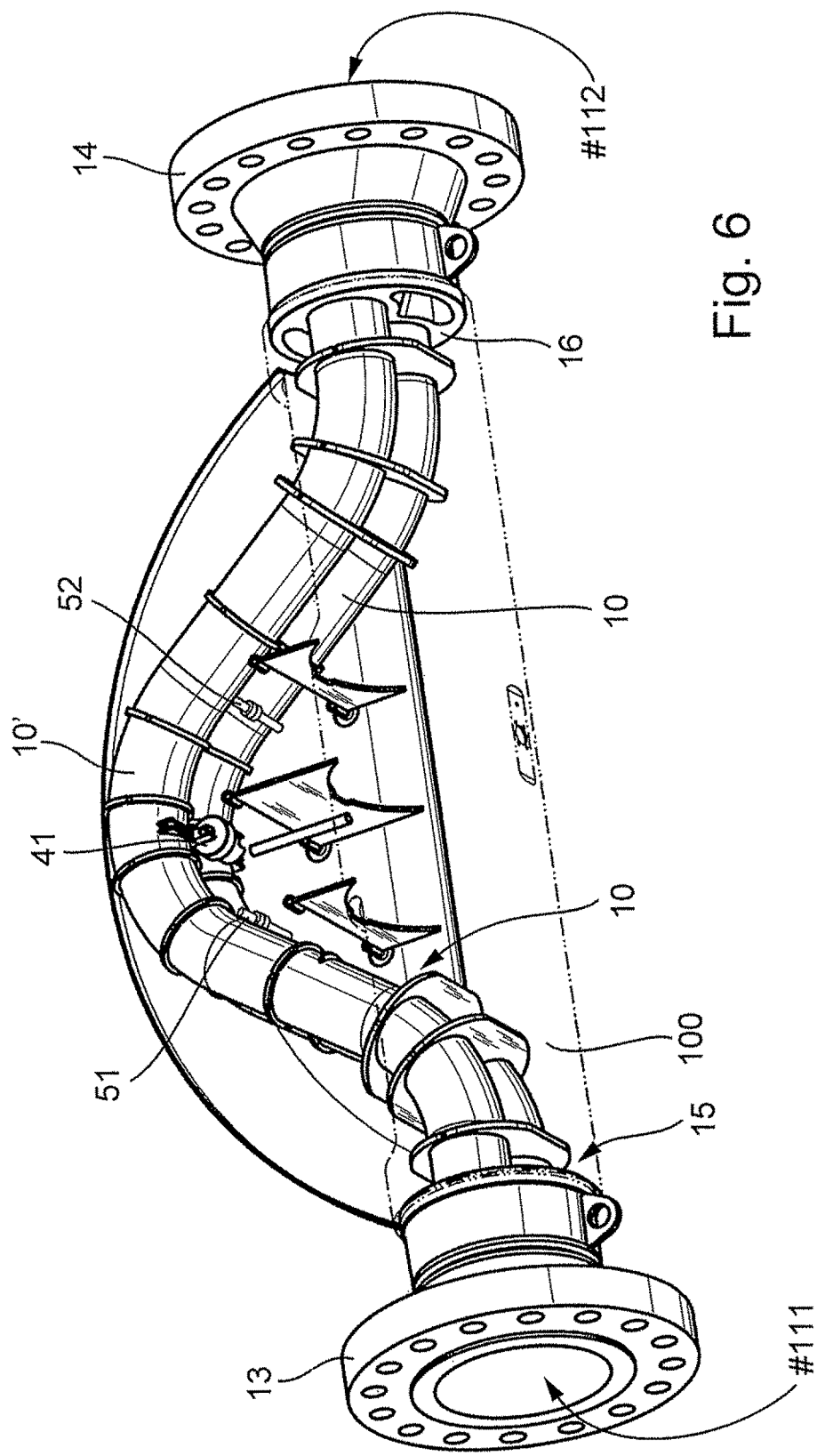
FIGS. 6, 7 in partially sectioned, or perspective, views, another variant of a measuring transducer of vibration-type, especially a measuring transducer suitable for a measuring system according to FIGS. 2a, 2b.
Figure 7:
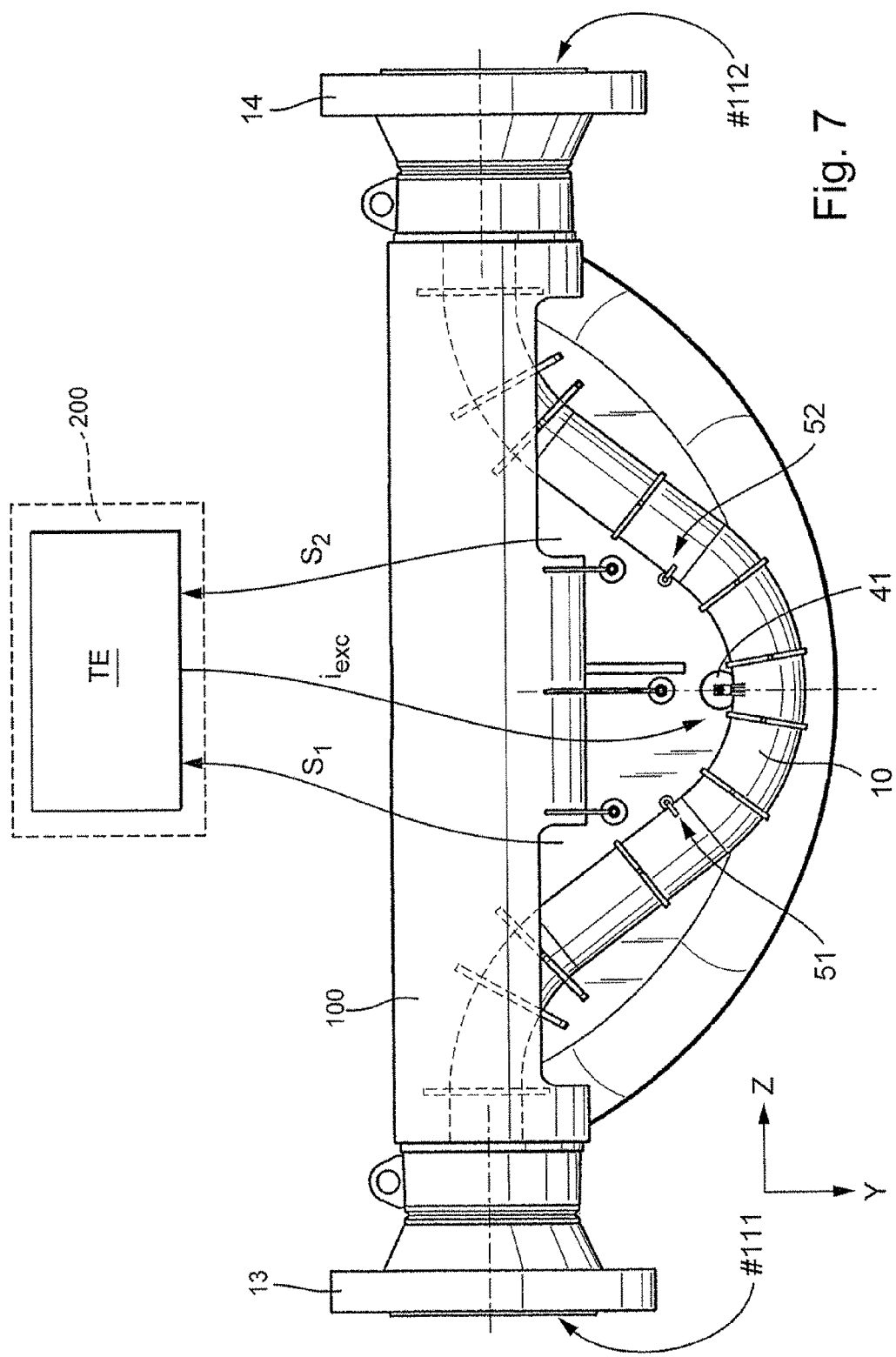

For conveying flowing medium, the inner part of the measuring transducer comprises generally at least a first—in the example of an embodiment illustrated in FIGS. 4 and 5, single, at least sectionally curved—measuring tube 10, which extends with an oscillatory length between an inlet-side, first measuring tube end 11# and an outlet-side, second measuring tube end 12# and which, for producing the aforementioned reaction forces during operation, is caused to vibrate at least over its oscillatory length and is, in such case, oscillatingly, repeatedly elastically deformed about a static rest position. The oscillatory length corresponds, in such case, to a length of an imaginary central- or also centroidal, axis extending within the lumen and forming an imaginary connecting line through the centers of gravity of all cross sectional areas of the measuring tube; in the case of a curved measuring tube, thus a stretched length of the measuring tube 10.

It is expressly noted here, that, although the measuring transducer in the example of an embodiment illustrated in FIGS. 4 and 5 has only a single, curved measuring tube and at least, insofar, resembles in its mechanical construction, as well as also in its principle of action that proposed in U.S. Pat. Nos. 7,360,451 or 6,666,098, or also that of measuring transducers available from the assignee under the type designation "PROMASS H", "PROMASS P" or "PROMASS S", of course, also measuring transducers with a straight and/or more than one measuring tube can serve for implementing the invention; compare, for instance, those designs disclosed in the initially mentioned U.S. Pat. Nos. 6,006,609, 6,513,393, 7,017,424, 6,840,109, 6,920,798, 5,796,011, 5,731,527 or 5,602,345 or, for example, also those measuring transducers available from the assignee under the type designation "PROMASS I", "PROMASS M", or "PROMASS E" or "PROMASS F", in each case, having two parallel measuring tubes. In accordance therewith, the measuring transducer can also have a single straight, measuring tube or at least two measuring tubes, for example, mechanically coupled with one another by means of an inlet-side flow divider and an outlet-side flow divider, in given cases, supplementally also by means of at least one inlet-side coupling element and at least one outlet-side coupling element, and/or equally constructed to one another and/or curved and/or parallel to one another, for conveying medium to be measured, and vibrating during operation, at least at times, for producing the primary signals, for instance, primary signals of an equal, shared oscillation frequency, however, of mutually opposite phase. In a further development of the invention, the measuring transducer, such as, for instance, schematically presented in FIGS. 6 and 7, consequently, has, supplementally to the first measuring tube 10, a second measuring tube 10', that is mechanically connected with the first measuring tube 10 for forming a first coupling zone on the inlet side by means of a, for example, plate-shaped, first coupling element and for forming a second coupling zone on the outlet side by means of a, for example, plate-shaped and/or, relative to the first coupling element, equally constructed, second coupling element. Also, in this case, thus the first coupling zone defines, in each case, an inlet-side, first measuring tube end 11#, 11'# of each of the two measuring tubes 10, 10' and the second coupling zone, in each case, an outlet-side, second measuring tube end 12#, 12'# of each of the two measuring tubes 10, 10'. Since, for the case, in which the inner part is formed by means of two measuring tubes, each of the two measuring tubes 10, 10' (especially measuring tubes 10, 10', which, during operation, oscillate with essentially opposite phase relative to one another and/or are mutually parallel and/or equally constructed as regards shape and material) serves for conveying medium to be measured, each of the two measuring tubes, in an additional embodiment of this second variant of the measuring transducer of the invention, opens on the inlet side into, in each case, one of two mutually spaced flow openings of a first flow divider 15 serving for dividing inflowing medium into two flow portions and on the outlet side into, in each case, one of two mutually spaced flow openings of a second flow divider 16 serving for guiding the flow portions back together, so that thus medium flows simultaneously and in parallel through the two measuring tubes during operation of the measuring system. In the example of an embodiment illustrated in FIGS. 6 and 7, the flow dividers are integral components of the measuring transducer housing, wherein the first flow divider forms an inlet-side, first housing end defining the inlet end #111 of the measuring transducer and the second flow divider forms an outlet-side, second housing end defining the outlet end #112 of the measuring transducer.

As directly evident from the combination of FIGS. 4 and 5, or 6 and 7, the at least one measuring tube 10 is, in each case, so formed, that the aforementioned center line lies, as quite usual in the case of measuring transducers of the type being discussed, in an imaginary tube plane of the measuring transducer. According to an embodiment of the invention, the at least one measuring tube 10 is, during operation, in such case, so caused to vibrate, that it oscillates, especially in a bending oscillation mode, about an oscillation axis, which is parallel to or coincident with an imaginary connecting axis imaginarily connecting the two measuring tube ends 11#, 12#. The at least one measuring tube 10 is additionally so formed and arranged in the measuring transducer, that the aforementioned connecting axis extends essentially parallel to, and, in given cases, also coincides with, an imaginary longitudinal axis L of the measuring transducers imaginarily connecting the in- and outlet ends of the measuring transducer.

The measuring transducer's at least one measuring tube 10, manufactured, for example, of stainless steel, titanium, tantalum, or zirconium or an alloy thereof, and, insofar, also an imaginary center line of the measuring tube 10 extending within its lumen, can be e.g. essentially U-shaped or, as well as also shown in FIGS. 4 and 5, or 6 and 7, essentially V-shaped. Since the measuring transducer should be applicable for a multitude of most varied applications, especially in the field of industrial measurements and automation technology, it is additionally provided, that the measuring tube, depending on application of the measuring transducer, has a diameter, which lies in the range extending between, for instance, 1 mm and, for instance, 100 mm.

For minimizing disturbing influences acting on an inner part formed by means of a single measuring tube, as well as also for reducing oscillatory energy totally released from a measuring transducer to the connected process line, the inner part of the measuring transducer comprises, according to the example of an embodiment illustrated in FIGS. 4 and 5, furthermore, a counteroscillator 20 mechanically coupled with the—in this case, single, curved—measuring tube 10 and embodied, for example, similarly as the measuring tube, with U-, or V-shape. Counteroscillator 20 is, as well as also shown in FIG. 2, arranged laterally spaced in the measuring transducer from the measuring tube 10 and affixed to the measuring tube 10 on the inlet side for forming a first coupling zone defining the aforementioned first measuring tube end 11#- and on the outlet side for forming a second coupling zone defining the aforementioned second measuring tube end 12#. Counteroscillator 20—here a counteroscillator extending essentially parallel to the measuring tube 10, and, in given cases, also arranged coaxially thereto—is produced from a metal compatible with the measuring tube as regards thermal expansion, such as, for instance, steel, titanium, or zirconium, and can, in such case, also be, for example, tubular or even essentially box-shaped. As shown in FIG. 2 or, among other things, also provided in U.S. Pat. No. 7,360,451, counteroscillator 20 can be formed, for example, by means of plates arranged on the left- and right sides of the measuring tube 10 or also by blind tubes arranged on the left- and right sides of the measuring tube 10. Alternatively thereto, the counteroscillator 20 can—as, for instance, provided in U.S. Pat. No. 6,666,098—also be formed by means of a single blind tube extending laterally of the measuring tube and parallel thereto. As evident from a combination of FIGS. 2 and 3, counteroscillator 20 is, in the example of an embodiment illustrated here, held to the first measuring tube end 11# by means of at least one inlet-side, first coupler 31 and to the second measuring tube end 12# by means of at least one outlet-side, second coupler 32, especially one essentially identical to the coupler 31. Serving as couplers 31, 32 can be, in such case, e.g. simple node plates, which are secured in appropriate manner on the inlet side and on the outlet side, in each case, to measuring tube 10 and to counteroscillator 20. Additionally,—as provided in the case of the example of an embodiment illustrated in FIGS. 2 and 3—a completely closed box, in each case, formed by means of node plates, mutually spaced in the direction of the imaginary longitudinal axis L of the measuring transducer, together with protruding ends of the counteroscillator 20 can serve on the inlet side and on the outlet side as coupler 31, or as coupler 32, as the case may be, or, in given cases, the counteroscillator can also be a partially open framework. As schematically presented in FIGS. 2 and 3, the measuring tube 10 is additionally connected via a straight, first connecting tube piece 11 opening on the inlet side in the region of the first coupling zone and via a straight, second connecting tube piece 12 opening on the outlet side in the region of the second coupling zone, especially a tube piece 12 essentially identical to the first connecting tube piece 11, to a process line (not shown) respectively supplying, and draining, the medium, wherein an inlet end of the inlet-side connecting tube piece 11 essentially forms the inlet end of the measuring transducer and an outlet end of the outlet-side connecting tube piece 12 forms the outlet end of the measuring transducer. In advantageous manner, the measuring tube 10, including the two connecting tube pieces 11, 12 can be one-piece, so that, for their manufacture, e.g. a single tubular stock, or semifinished part, of a material usual for such measuring transducers, such as e.g. stainless steel, titanium, zirconium, tantalum or corresponding alloys thereof, can serve. Instead of the measuring tube 10, inlet tube piece 11 and outlet tube piece 12, in each case, being segments of a single, one piece tube, these can, in case required, however, also be produced by means of individual stock, or semifinished parts, which are subsequently joined together, e.g. welded together. In the example of an embodiment illustrated in FIGS. 2 and 3, it is additionally provided, that the two connecting tube pieces 11, 12, are so oriented relative to one another as well as to an imaginary longitudinal axis L of the measuring transducer imaginarily connecting the two coupling zones 11#, 12#, that the inner part formed here by means of counteroscillator and measuring tube can, accompanied by twistings of the two connecting tube pieces 11, 12, move like a pendulum about the longitudinal axis L. For such purpose, the two connecting tube pieces 11, 12 are so oriented relative to one another, that the essentially straight tube segments extend essentially parallel to the imaginary longitudinal axis L, or to the imaginary oscillation axis of the bending oscillations of the measuring tube, such that the tube segments essentially align both with the longitudinal axis L as well as also with one another. Since the two connecting tube pieces 11, 12 in the example of an embodiment illustrated here are essentially straight over their entire length, they are, accordingly, as a whole, oriented essentially aligned with one another as well as with the imaginary longitudinal axis L. As furthermore evident from FIGS. 2 and 3, the measuring transducer housing 100 is bending- and torsion-stiffly, especially rigidly, especially in comparison to the measuring tube 10, affixed to an, as regards the first coupling zone, distal inlet end of the inlet-side connecting tube piece 11 as well as to an, as regards the first coupling zone, distal outlet end of the outlet-side connecting tube piece 12. Insofar, thus the entire inner part—here formed by means of measuring tube 10 and counteroscillator 20—is not only completely encased by the measuring transducer housing 100, but, also, as a result of its eigenmass and the spring action of both connecting tube pieces 11, 12, also oscillatably held in the measuring transducer housing 100.

For the typical case, in which the measuring transducer MT is to be assembled releasably with the process line, for example, a process line in the form of a metal pipeline, the measuring transducer has on the inlet side a first connecting flange 13 for connection to a line segment of the process line supplying medium to the measuring transducer and on the outlet side a second connecting flange 14 for connection to a line segment of the process line removing medium from the measuring transducer. The connecting flanges 13, 14 can, in such case, as quite usual in the case of measuring transducers of the described type, also be integrated terminally into the measuring transducer housing 100. In case required, the connecting tube pieces 11, 12, can, moreover, however, also be connected directly with the process line, e.g. by means of welding or hard soldering. In the example of an embodiment illustrated in FIGS. 2 and 3, the first connecting flange 13 is formed on the inlet-side connecting tube piece 11 on its inlet end and the second connecting flange 14 on the outlet-side connecting tube piece 12 on its outlet end, while, in the example of an embodiment illustrated in FIGS. 4 and 5, the connecting flanges are correspondingly connected with the associated flow dividers.

For active exciting of mechanical oscillations of the at least one measuring tube, or the measuring tubes, as the case may be, especially at one or more of its, or their, natural eigenfrequencies, each of the measuring transducers illustrated in FIGS. 4 to 7 additionally comprises an electromechanical, especially an electrodynamic (thus formed by means of a plunging armature, coil pair, or solenoid), exciter mechanism 40. This serves—operated by a correspondingly conditioned, exciter signal, e.g. having a controlled electrical current and/or a controlled voltage, delivered by the driver circuit of the transmitter electronics and, in given cases, in the interaction with the measuring—and evaluating-circuit—, in each case, to convert, electrical exciter energy, or power $E_{exc}$, fed by means of the driver circuit into an exciter force $F_{exc}$ acting, e.g. with pulse shape or harmonically, on the at least one measuring tube 10 and deflecting such in the above-described manner. The exciter force $F_{exc}$ can, as usual in the case of such measuring transducers, be bidirectional or unidirectional and can be tuned in manner known to those skilled in the art, e.g. by means of an electrical current, and/or voltage, control circuit, as regards its amplitude and, e.g. by means of a phase control loop, as regards its frequency. Serving as exciter mechanism 40 can be e.g. an exciter mechanism 40 formed in conventional manner by means of an oscillation exciter 41—, for example, a single electrodynamic oscillation exciter—acting centrally, thus in the region of half of an oscillatory length, on the respective measuring tube. The oscillation exciter 41 can, in the case of an inner part formed by means of counteroscillator and measuring tube, as shown in FIG. 4, for example, be formed by means of, secured on the counteroscillator 20, a cylindrical exciter coil, through which, during operation, a corresponding exciter current flows and which, associated therewith, is permeated by a corresponding magnetic field, as well as, at least partially plunging into the exciter coil, a permanently magnetic armature, which is affixed externally, especially at half-length, to the measuring tube 10. Other exciter mechanisms also quite suitable for the measuring system of the invention for oscillating the at least one measuring tube are shown e.g. in the initially mentioned U.S. Pat. Nos. 5,705,754, 5,531,126, 6,223,605, 6,666,098 or 7,360,451.

According to an additional embodiment of the invention, the at least one measuring tube 10 is actively excited during operation by means of the exciter mechanism, at least at times, in a wanted mode, in which it, especially predominantly or exclusively, executes bending oscillations about the mentioned imaginary oscillation axis, for example, predominantly with exactly a natural eigenfrequency (resonance frequency) of the particular, or the therewith, in each case, formed, inner part of the measuring transducer, such as, for instance, that, which corresponds to a bending oscillation fundamental mode, in which the at least one measuring tube has exactly one oscillatory antinode. Especially, in such case, it is additionally provided, that the at least one measuring tube 10, as quite usual in the case of such measuring transducers with curved measuring tube, is so excited by means of the exciter mechanism to bending oscillations at an exciter frequency $f_{exc}$, that it bends out in the wanted mode about the mentioned imaginary oscillation axis—, for instance, in the manner of a unilaterally clamped cantilever—oscillatingly, at least partially according to one of its natural bending oscillation forms. The bending oscillations of the measuring tube have, in such case, in the region of the inlet-side coupling zone defining the inlet-side measuring tube end 11#, an inlet-side oscillation node and, in the region of the outlet-side coupling zone defining the outlet-side measuring tube end 12#, an outlet-side oscillation node, so that thus the measuring tube extends with its oscillatory length essentially freely oscillating between these two oscillation nodes. In case required, the vibrating measuring tube can, however, also, as, for example, provided in U.S. Pat. No. 7,077,014 or JP-A 9-015015, be influenced, with targeting, as regards its oscillatory movements by means of resilient and/or electromotive, coupling elements acting supplementally correspondingly in the region of the oscillatory length of the measuring tube. The driver circuit can be embodied e.g. as a phase control loop (PLL, or phase locked loop), which is used in manner known to those skilled in the art to keep an exciter frequency, $f_{exc}$, of the exciter signal continually at the instantaneous eigenfrequency of the desired wanted mode. Construction and application of such phase control loops for active exciting of measuring tubes to oscillations at mechanical eigenfrequencies is described at length e.g. in U.S. Pat. No. 4,801,897. Of course, also other driver circuits suitable for tuning the exciter energy, $E_{exc}$, and known, per se, to those skilled in the art can be used, for example, also those mentioned in the initially set-forth state of the art, for instance, the initially mentioned U.S. Pat. Nos. 4,777,833, 4,801,897, 4,879,911, 5,009,109, 5,024,104, 5,050,439, 5,804,741, 5,869,770, 6,073,495 or 6,311,136. Additionally, as regards an application of such driver circuits for measuring transducers of vibration-type, reference is made to the transmitter electronics provided with measurement transmitters of the series "PROMASS 83", as available from the assignee, for example, in connection with measuring transducers of the series "PROMASS E", "PROMASS F", "PROMASS H", "PROMASS I", "PROMASS P" or "PROMASS S". Their driver circuit is, for example, in each case, so executed, that the lateral bending oscillations in the wanted mode are controlled to a constant amplitude, thus also largely independent of the density, ρ.

For causing the at least one measuring tube 10 to vibrate, the exciter mechanism 40, as already mentioned, is fed by means of a likewise oscillating exciter signal of adjustable exciter frequency, $f_{exc}$, so that an exciter current $i_{exc}$ appropriately controlled in its amplitude flows during operation through the exciter coil of the, here, single oscillation exciter acting on the measuring tube 10, whereby the magnetic field required for moving the measuring tube is produced. The driver, or also exciter, signal, or its exciter current $i_{exc}$ can e.g. be harmonically, multifrequently or also rectangularly formed. The exciter frequency, $f_{exc}$, of the exciter current required for maintaining the bending oscillations of the at least one measuring tube 10, in the case of the measuring transducer illustrated in the example of an embodiment, can, in advantageous manner, be so selected and set, that the laterally oscillating measuring tube 10 oscillates at least predominantly in a bending oscillation, fundamental mode having a single oscillatory antinode. In accordance therewith, according to an additional embodiment of the invention, the exciter, or also wanted mode, frequency, $f_{exc}$, is so set, that it corresponds, as exactly as possible, to an eigenfrequency of bending oscillations of the measuring tube 10, especially that of the bending oscillation, fundamental mode. In the case of application of a measuring tube manufactured of stainless steel, especially Hastelloy, having a caliber of 29 mm, a wall thicknesss of, for instance, 1.5 mm, an oscillatory length of, for instance, 420 mm and a chordal length, measured between the two measuring tube ends, of 305 mm, the resonance frequency of the same corresponding to the bending oscillation, fundamental mode, for example, in the case of a density of practically zero, e.g. in the case of a measuring tube filled only with air, would be, for instance, 490 Hz.

In the example of an embodiment illustrated in FIGS. 4 and 5 having an inner part formed by means of measuring tube and counteroscillator, the measuring tube 10 executes bending oscillations actively excited by means of the exciter mechanism predominantly relative to the counteroscillator 20, especially at a shared oscillation frequency and mutually opposite phases. In the case of an exciter mechanism acting simultaneously, for example, differentially, both on the measuring tube as well as also on the counteroscillator, in such case, also the counteroscillator 20 is excited simultaneously to cantilever oscillations, and, indeed, such that it oscillates with equal frequency, however, at least partially out of phase, especially with essentially opposite phase, to the measuring tube 10 oscillating in the wanted mode. Especially, measuring tube 10 and counteroscillator 20 are, in such case, additionally so matched to one another, or so excited, that they execute during operation, at least at times and at least partially, bending oscillations opposite-equally, thus with equal-frequency, however, essentially opposite phase, about the longitudinal axis L. The bending oscillations can, in such case, be so embodied, that they are of equal modal order and, thus, at least in the case of resting fluid, essentially equally shaped; in the other case of application of two measuring tubes, these are, as usual in the case of measuring transducers of the type being discussed, actively so excited by means of the exciter mechanism, especially one acting differentially between the two measuring tubes 10, 10', that they execute during operation, at least at times, opposite-equal bending oscillations around the longitudinal axis L. In other words, the two measuring tubes 10, 10', or measuring tube 10 and counteroscillator 20, move then, in each case, relative to one another in the manner of oscillating tuning fork tines. For this case, according to an additional embodiment of the invention, the at least one electro-mechanical, oscillation exciter is designed to excite, and, respectively, to maintain, opposite-equal vibrations of the first measuring tube and the second measuring tube, especially bending oscillations of each of the measuring tubes, each about an imaginary oscillation axis imaginarily connecting the relevant first measuring tube end and the relevant second measuring tube end.

For the operationally provided case, in which the medium is flowing in the process line and, thus, the mass flow m is different from zero, also Coriolis forces are induced in the medium by means of the measuring tube 10 vibrating in the above described manner. The Coriolis forces, in turn, act on the measuring tube 10 and so effect an additional deformation of the same, which is registerable by sensor. The deformation occurs essentially according to an additional natural eigenoscillation form of higher modal order than the wanted mode. An instantaneous feature of this so-called Coriolis mode superimposed with equal frequency on the excited wanted mode is, in such case, especially as regards amplitude, also dependent on the instantaneous mass flow m. Serving as Coriolis mode, as usual in the case of such measuring transducers with curved measuring tube, can be e.g. the eigenoscillation form of the anti-symmetric twist mode, thus that, in the case of which the measuring tube 10, as already mentioned, also executes rotary oscillations about an imaginary rotary oscillation axis directed perpendicular to the bending oscillation axis and imaginarily intersecting the center line of the measuring tube 10 in the region of half the oscillatory length.

For registering oscillations, especially bending oscillations, of the at least one measuring tube 10, especially also those in the Coriolis mode, the measuring transducer additionally includes, in each case, a corresponding sensor arrangement 50. The sensor arrangement comprises, as also schematically presented in FIGS. 4 to 7, arranged spaced from the at least one oscillation exciter on the at least one measuring tube 10, for example, an electrodynamic, first oscillation sensor 51, which delivers a first primary signal $s_1$ of the measuring transducer representing vibrations of the measuring tube 10, for example, a voltage corresponding to the oscillations or an electrical current corresponding to the oscillations, as well as arranged spaced from the first oscillation sensor 51 on the at least one measuring tube 10, an especially electrodynamic, second oscillation sensor 52, which delivers a second primary signal $s_2$ of the measuring transducer representing vibrations of the measuring tube 10. A length of the region of the associated at least one measuring tube extending between the two, for example, equally constructed, oscillation sensors, especially an essentially freely oscillatingly vibrating region, corresponds, in such case, to a measuring length of the respective measuring transducer. Each of the—typically broadband—primary signals $s_1$, $s_2$ of the measuring transducer MT has, in such case, in each case, a signal component corresponding to the wanted mode and having a signal frequency corresponding to the instantaneous oscillation frequency, $f_{exc}$, of the at least one measuring tube 10 oscillating in the actively excited, wanted mode and a phase shift dependent on the current mass flow of the medium flowing in the at least one measuring tube 10 and measured relative to the exciter signal $i_{exc}$, generated, for example, by means of the PLL-circuit as a function of a phase difference existing between at least one of the oscillation measurement signals $s_1$, $s_2$ and the exciter current in the exciter mechanism. Even in the case of application of a rather broadband exciter signal $i_{exc}$, as a result of the most often very high oscillation quality factor of the measuring transducer MT, it can be assumed therefrom, that the signal component of each of the primary signals corresponding with the wanted mode predominates over other signal components, especially signal components corresponding to possible external disturbances and/or classified as noise, and, insofar, is dominating also at least within a frequency range corresponding to a bandwidth of the wanted mode.

In the here illustrated examples of embodiments, in each case, the first oscillation sensor 51 is arranged on the inlet side and the second oscillation sensor 52 on the outlet side on the at least one measuring tube 10, especially with the second oscillation sensor 52 being equally widely spaced from the at least one oscillation exciter, or from the half length plane, of the measuring tube 10 as is the first oscillation sensor 51. As quite usual in the case of such measuring transducers of vibration-type used in measuring systems formed as Coriolis, mass flow measuring devices, the first oscillation sensor 51 and the second oscillation sensor 52 are, according to an embodiment of the invention, additionally arranged in the measuring transducer, in each case, on a side of the measuring tube occupied by the oscillation exciter 41. Furthermore, also the second oscillation sensor 52 can be arranged in the measuring transducer on the side of the measuring tube occupied by the first oscillation sensor 51. The oscillation sensors of the sensor arrangement can, in advantageous manner, additionally be so embodied, that they deliver the same type of primary signals, for example, in each case, a signal voltage, or a signal current. In an additional embodiment of the invention, both the first oscillation sensor as well as also the second oscillation sensor are additionally, in each case, so placed in the measuring transducer MT, that each of the oscillation sensors registers, at least predominantly, vibrations of the at least one measuring tube 10. For the above described case, in which the inner part is formed by means of a measuring tube and a counteroscillator coupled therewith, according to an additional embodiment of the invention, both the first oscillation sensor as well as also the second oscillation sensor are so embodied and so placed in the measuring transducer, that each of the oscillation sensors registers, for example, differentially, predominantly oscillations of the measuring tube relative to the counteroscillator, such that thus both the first primary signal $s_1$ as well as also the second primary signal $s_2$, represent oscillatory movements, especially opposite-equal, oscillatory movements, of the at least one measuring tube 10 relative to the counteroscillator 20. For the other described case, in which the inner part is formed by means of two measuring tubes, especially measuring tubes oscillating opposite-equally during operation, according to another embodiment of the invention, both the first oscillation sensor as well as also the second oscillation sensor are so embodied and so placed in the measuring transducer, that each of the oscillation sensors predominantly registers, for example, differentially, oscillations of the first measuring tube 10 relative to the second measuring tube 10', that thus both the first primary signal $s_1$ as well as also the second primary signal $s_2$ represent, especially opposite-equally, oscillatory movements of the two measuring tubes relative to one another, especially in such a manner that—as usual in the case of conventional measuring transducers—the first primary signal produced by means of the first oscillation sensor represents inlet-side vibrations of the first measuring tube relative to the second measuring tube and the second primary signal produced by means of the second oscillation sensor represents outlet-side vibrations of the first measuring tube relative to the second measuring tube. In an additional embodiment of the invention, it is additionally provided, that the sensor arrangement has exactly two oscillation sensors, thus supplementally to the first and second oscillation sensors there are no additional oscillation sensors, and, insofar, as regards the used components thus corresponds to a conventional sensor arrangement.

The oscillation measurement signals $s_1, s_2$, delivered by the sensor arrangement, serving as primary signals of the measuring transducer, and having, in each case, a signal component signal frequency corresponding with an instantaneous oscillation frequency, $f_{exc}$, of the at least one measuring tube 10 oscillating in the actively excited wanted mode, are, as also shown in FIG. 3, fed to the transmitter electronics TE and @ there then to the therein provided measuring- and evaluating circuit μC. First, they are preprocessed, especially preamplified, filtered and digitized, by means of a corresponding input circuit IE, in order then to be able to be suitably evaluated. As input circuit IE, as well as also as measuring- and evaluating circuit μC, there can be applied, in such case, circuit technologies (for example, also such circuits according to the initially mentioned state of the art) already applied and established in conventional Coriolis, mass flow measuring devices for the purpose of converting the primary signals, or of ascertaining mass flow rates and/or totalled mass flows, etc. According to an additional embodiment of the invention, the measuring- and evaluating circuit μC is accordingly also implemented by means of a microcomputer, for example, a digital signal processor (DSP), provided in the transmitter electronics TE, and by means of program-code correspondingly implemented, and running, therein. The program-code can be stored persistently e.g. in a non-volatile, data memory EEPROM of the microcomputer and, on the starting of the same, loaded into a volatile data memory RAM, e.g. integrated in the microcomputer. For such applications, suitable processors include e.g. such of type TMS320VC33, as available from the firm, Texas Instruments Inc. Of course, the primary signals $s_1, s_2$, are, as already indicated, to be converted into corresponding digital signals by means of corresponding analog-to-digital converters A/D of the transmitter electronics TE for processing in the microcomputer; compare, for this, for example, the initially mentioned U.S. Pat. Nos. 6,311,136 or 6,073,495 or also the aforementioned measurement transmitters of the series "PROMASS 83".

In the case of the measuring system of the invention, the transmitter electronics TE serves, especially, to measure, by means of the first primary signal and by means of the second primary signal as well as taking into consideration a Reynolds number ascertained for the flowing medium, a pressure difference, such as e.g. a pressure drop caused by the measuring transducer, occurring between two predetermined reference points in the flowing medium, for example, also points located within the measuring transducer. For such purpose, the transmitter electronics generates, by means of the first and second primary signals as well as with application of an internally held (for instance, in the volatile data memory RAM) Reynolds number, measured value $X_{Re}$, which represents a Reynolds number, Re, for medium flowing in the measuring transducer, during operation, recurringly, a pressure difference, measured value $X_{\Delta p}$, which correspondingly represents the aforementioned pressure difference, for example, in such a manner, that a first of the two reference points is located in the measuring transducer on the inlet side and a second of the two reference points in the measuring transducer on the outlet side and, insofar, a pressure difference, $\Delta p_{total}$, falling across the measuring transducer, as a whole, is ascertained. The Reynolds number, measured value $X_{Re}$ can, for example, be generated during operation by means of the driver signal and/or by means of at least one of the primary signals, for example, according to the method described in the initially mentioned U.S. Pat. No. 6,513,393, directly in the transmitter electronics TE. Alternatively thereto or in supplementation thereof, the Reynolds number, measured value $X_{Re}$, can, however, for example, also be transmitted by the mentioned electronic data processing system to the transmitter electronics TE.

Figure 8:
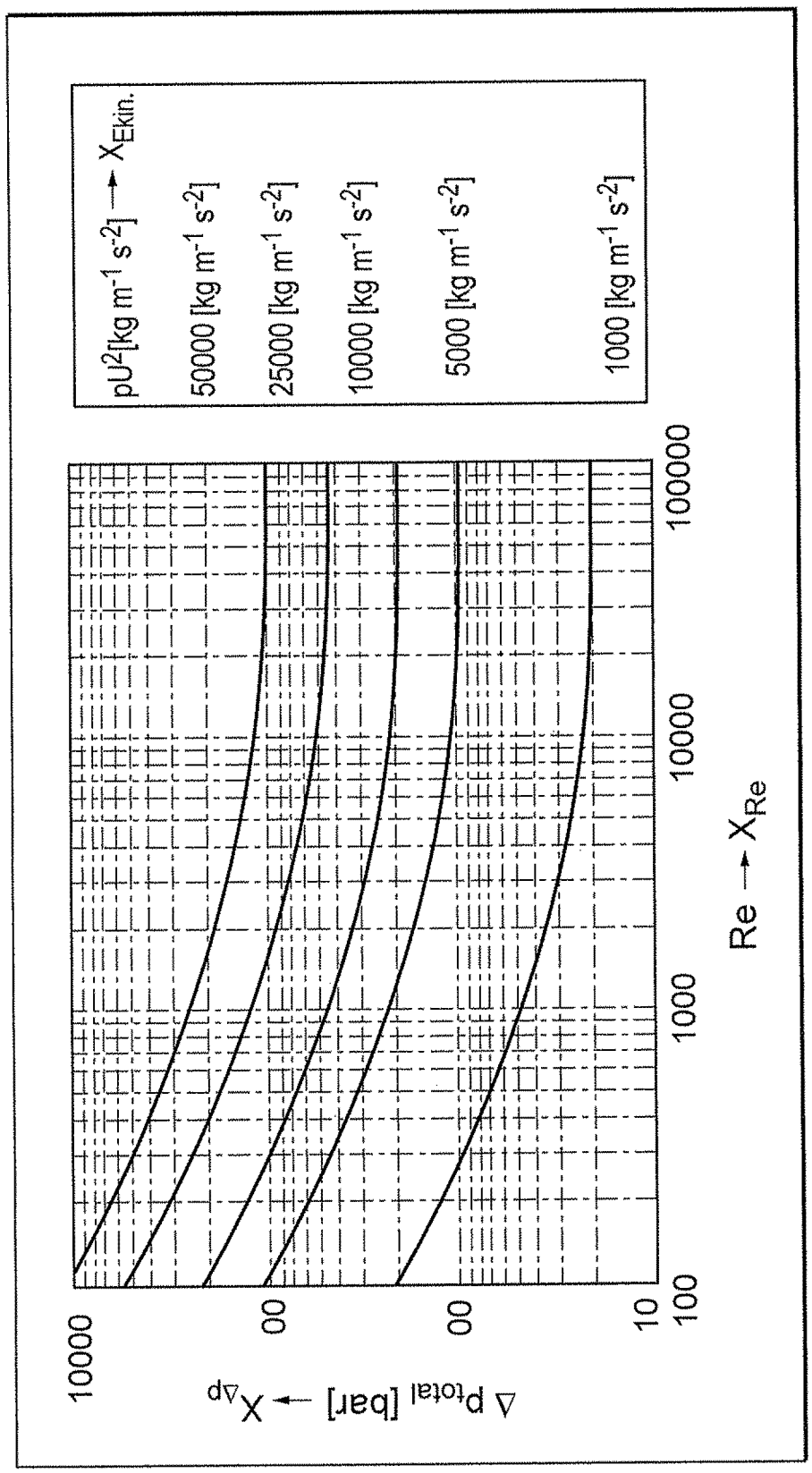
FIGS. 8 to 11 results of experimental investigations performed in connection with the invention, especially results obtained with application of computer based simulation programs and/or results obtained by means of real measuring systems in the laboratory, or characteristic curves derived therefrom, serving for ascertaining pressure difference in a medium flowing through a measuring transducer of vibration-type—, for instance, one according to FIG. 4, 5, or 6, 7.
Figure 9:
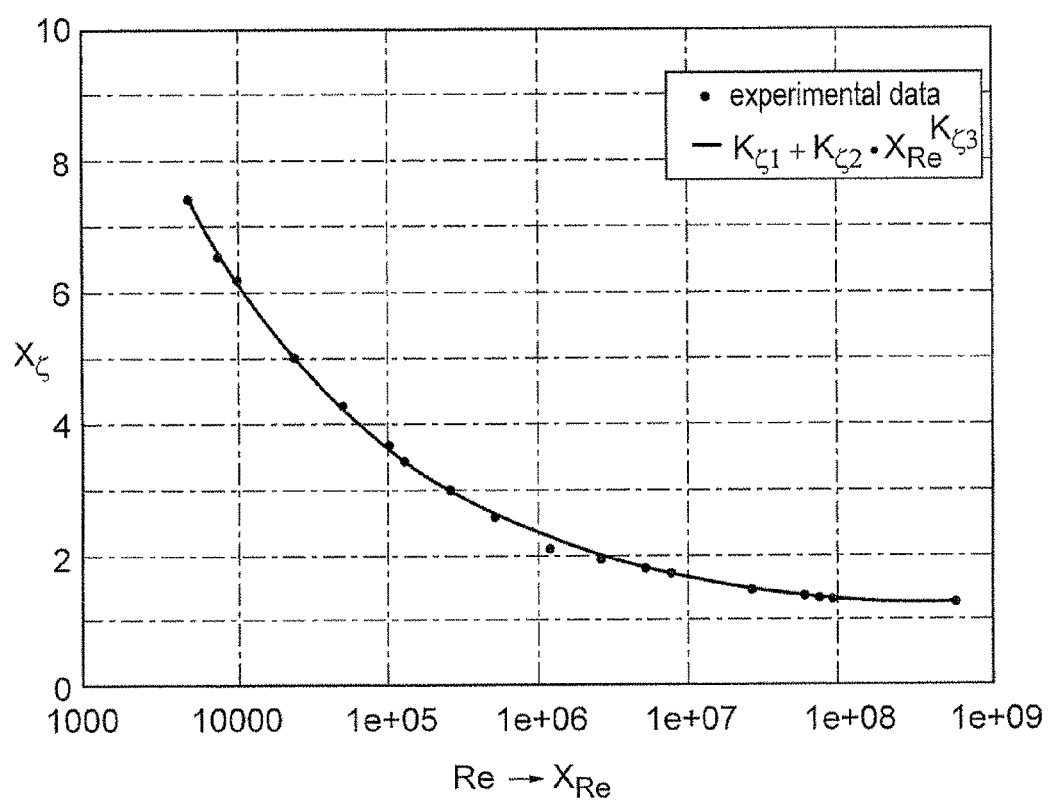
Figure 10:
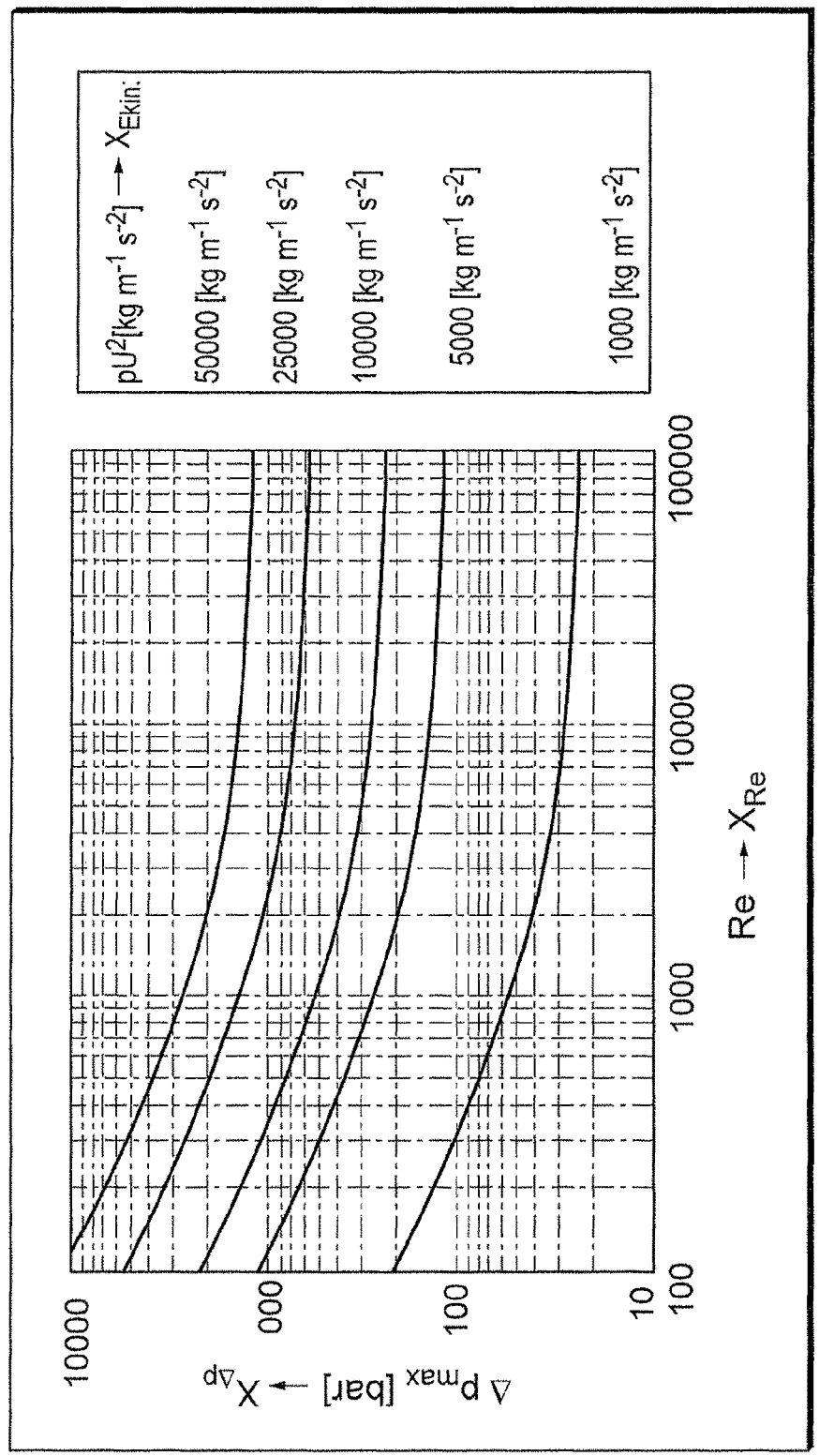
Figure 11:
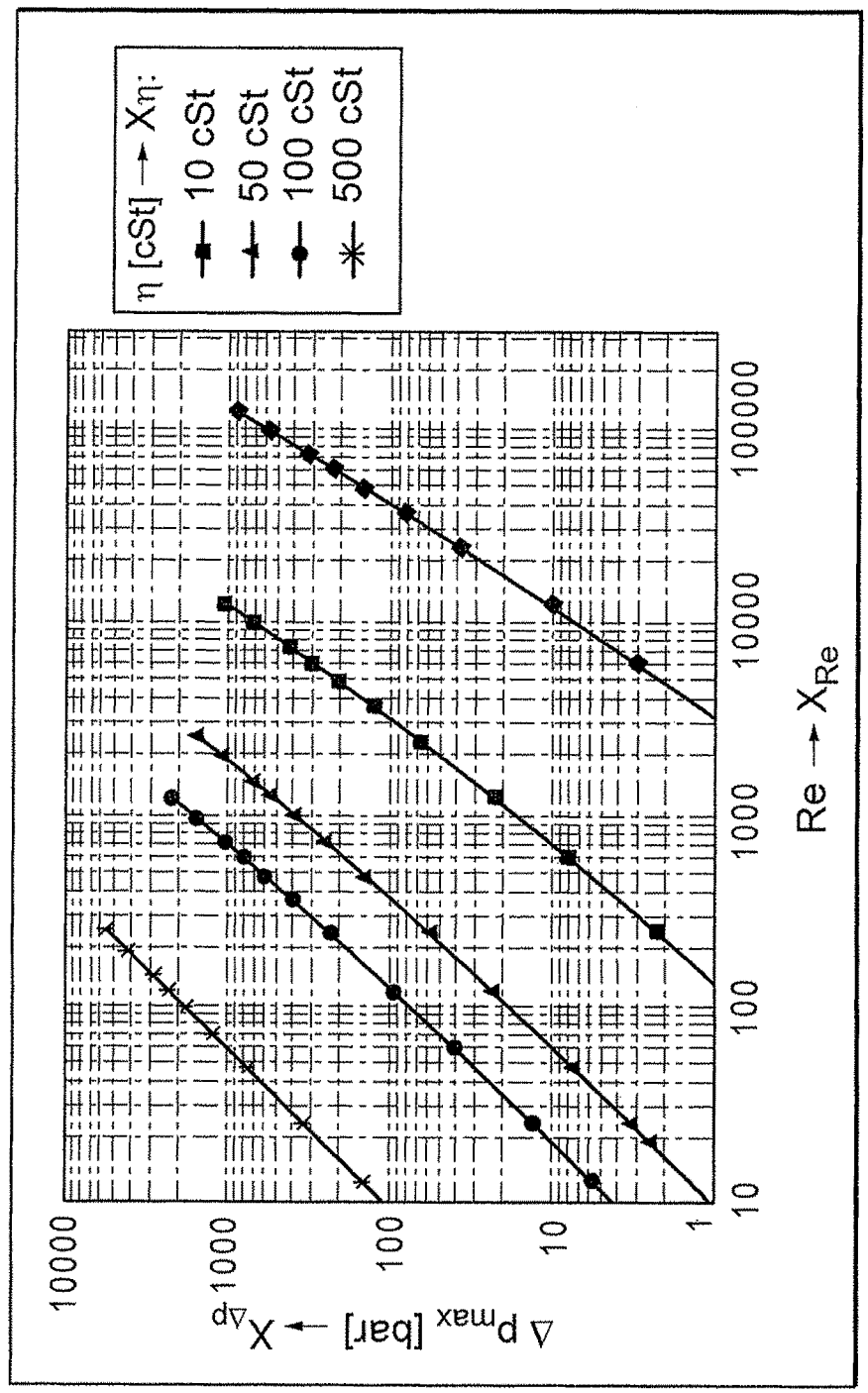
Figure 12:
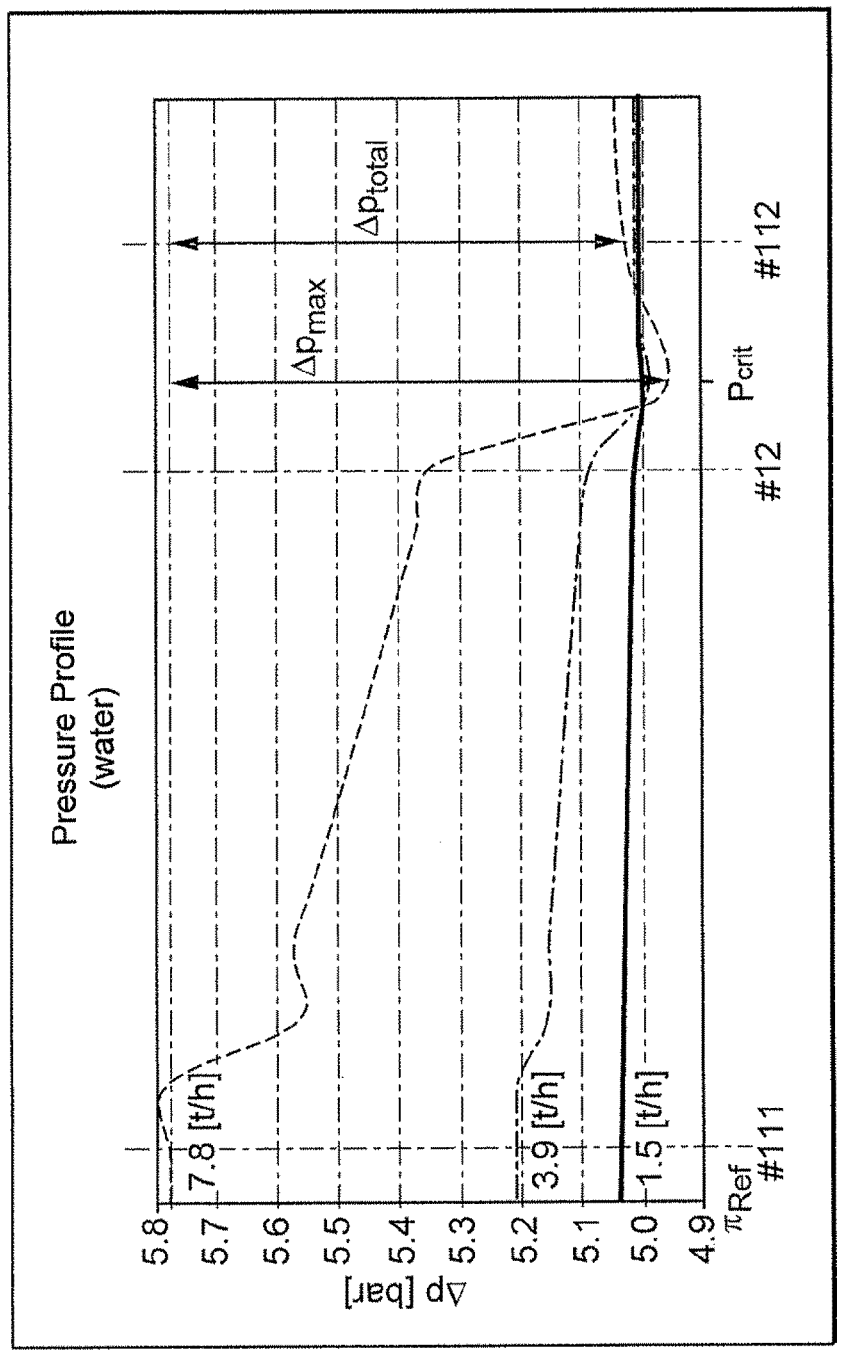
FIG. 12 experimentally ascertained pressure loss profiles in a conventional measuring transducer of vibration-type, especially such obtained with application of computer based simulation programs.

In an additional embodiment of the invention, the transmitter electronics ascertains the pressure difference, measured value with application of the Reynolds number, measured value $X_{Re}$ as well as a likewise measuring system internally held (for example, again, in the volatile data memory RAM), flow energy, measured value $X_{Ekin}$, which represents a kinetic energy, $\rho U^2$, of medium flowing in the measuring transducer dependent on a density, $\rho$, and a flow velocity, U, of the medium flowing in the measuring transducer. For such purpose, there is implemented in the transmitter electronics additionally a corresponding computing algorithm, which generates the pressure difference, measured value based on the relationship (illustrated in FIG. 8, by way of example), $X_{\Delta p} = (K_{\zeta,1} + K_{\zeta,2} \cdot X_{Re}^{K_{\zeta,3}}) \cdot X_{Ekin}$, wherein $K_{\zeta,1}, K_{\zeta,2}, K_{\zeta,3}$, are earlier experimentally ascertained (for instance, in the course of a calibrating of the measuring system and/or by means of computer based calculations, e.g. by means of FEM, or CFD, and kept, especially as constants, in the transmitter electronics) measuring system parameters, which lastly also define the respective sites of the reference points underpinning the pressure difference to be ascertained. The function formed by means of these measuring system parameters (an example of such a function ascertained by experimental investigations is shown in FIG. 9) represents quasi a pressure drop characteristic curve of the measuring system mediating between the instantaneous, or currently valid, Reynolds number Re of the flowing medium and a thereon dependent, specific pressure drop referenced to the instantaneous kinetic energy, $\rho U^2$, of the medium flowing in the measuring transducer. The function values $X_\zeta = K_{\zeta,1} + K_{\zeta,2} \cdot X_{Re}^{K_{\zeta,3}}$ generated internally in the transmitter electronics from the pressure drop characteristic curve and referenced subsequently herein as the pressure drop coefficients $X_\zeta$, depend only on the instantaneous Reynolds number. The measuring system parameters $K_{\zeta,1}, K_{\zeta,2}, K_{\zeta,3}$ defining the pressure drop, characteristic curve can, for example, be so selected, that a first of the reference points is located in the inlet end #111 (here formed by the first housing end of the measuring transducer housing) of the measuring transducer, and that a second of the reference points is located in the outlet end #112 (here formed by the second housing end of the measuring transducer housing) of the measuring transducer, so that thus the pressure difference, measured value $X_{\Delta p}$, as a result, represents a total pressure difference, $\Delta p_{total}$, occurring in the flowing medium from the inlet end to the outlet end; compare FIGS. 9 and 11. The measuring system parameters and, insofar, the reference points can, for example, however, also be so selected, that the pressure difference, measured value $X_{\Delta p}$, as shown in FIG. 10, represents a maximal pressure drop, $\Delta p_{max}$, in the medium flowing within the measuring transducer. This maximum pressure drop, $\Delta p_{max}$, arises, as also evident from the pressure loss profiles illustrated, by way of example, in FIG. 12 for measuring transducers of the type being discussed, between the inlet end #111 of the measuring transducer formed by the first housing end and a region of increased turbulence located upstream of the outlet end #112 of the measuring transducer formed by the second housing end. Taking into consideration the pressure drop, characteristic curve, or the pressure drop coefficients $X_\zeta$, the functional relationship proposed for ascertaining the pressure difference, measured value, can, furthermore, be simplified to the relationship $X_{\Delta p} = X_\zeta \cdot X_{Ekin}$.

The measuring- and evaluating circuit μC serves according to an additional embodiment of the invention additionally (for the purpose of ascertaining the pressure difference, measured value $X_{\Delta p}$, especially also for ascertaining the therefor required, flow energy, measured value $X_{Ekin}$, and/or the therefor required, Reynolds number, measured value $X_{Re}$, with application of the primary signals $s_1$, $s_2$, delivered by the sensor arrangement 50, for example, on the basis of a phase difference detected between the primary signals $s_1$, $s_2$ of the first and second oscillation sensors 51, 52, generated in the case of measuring tube 10 oscillating partially in wanted- and Coriolis modes) to ascertain, recurringly, a mass flow, measured value $X_m$, which represents, as exactly as possible, the mass flow rate, ṁ, to be measured for the medium guided through the measuring transducer. For such purpose, the measuring- and evaluating circuit produces, according to an additional embodiment of the invention, during operation, recurringly, a phase difference, measured value $X_{\Delta\phi}$, which instantaneously represents the phase difference, $\Delta\phi$, existing between the first primary signal $s_1$ and the second primary signal $s_2$. The calculation of the mass flow, measured value $X_m$ can occur, with application of a frequency, measured value $X_f$, likewise held in the transmitter electronics, and representing an oscillation frequency of vibrations, for example, the above mentioned lateral bending oscillations of the at least one measuring tube 10 in the wanted mode, for example, based on the known relationship:

$$X_m = K_m \cdot \frac{X_{\Delta\varphi}}{X_f}$$

wherein $K_m$ is an earlier experimentally ascertained (e.g. ascertained in the course of calibrating the measuring system and/or by means of computer based calculations, and internally kept as a constant e.g. in the non-volatile data memory), measuring system parameter, which correspondingly mediates between the quotient, formed here by means of the phase difference, measured value $X_{\Delta\phi}$ and the frequency, measured value $X_f$, and the mass flow rate, ṁ, to be measured. The frequency, measured value $X_f$ can be ascertained, in simple manner, e.g. on the basis of the primary signals delivered by the sensor arrangement or also on the basis of the at least one driver signal feeding the exciter mechanism, in manner known to those skilled in the art.

In an additional embodiment, it is further provided, that the transmitter electronics stores, for example, in the volatile data memory RAM, a density, measured value $X_\rho$, which represents instantaneously a density, ρ, to be measured for the medium, and/or a viscosity, measured value $X_\eta$, which represents instantaneously a viscosity of the medium. Based on the mass flow, measured value $X_m$ and the density, measured value $X_\rho$, by means of the transmitter electronics, the flow energy, measured value $X_{Ekin}$ required for ascertaining the pressure difference, measured value $X_{\Delta p}$, can be internally ascertained, for instance, by means of the relationship $$X_{Ekin} = K_{Ekin} \cdot \frac{(X_m)^2}{X_\rho},$$

while, with application of the mass flow, measured value $X_m$ and the viscosity, measured value $X_\eta$, in simple manner, the Reynolds number, measured value $X_{Re}$ required for ascertaining the pressure difference, measured value $X_{\Delta p}$ can be ascertained in the transmitter electronics, for instance, based on the relationship $$X_{Re} = K_{Re} \cdot \frac{X_m}{X_\eta}.$$

The corresponding measuring system parameters $K_{Ekin}$, and $K_{re}$, respectively, are essentially dependent on the effective flow cross section of the measuring transducer and can be earlier directly experimentally ascertained, e.g., again, in the course of a calibrating of the measuring system and/or by means of computer based calculations, and stored in the transmitter electronics as measuring system specific constants.

Taking into consideration the aforementioned functional relationships, the pressure difference, measured value $X_{\Delta p}$ can also be ascertained based on one of the following relationships:

$$X_{\Delta p} = X_\zeta \cdot K_{Ekin} \cdot \frac{(X_m)^2}{X_\rho},$$

$$X_{\Delta p} = \left( K_{\zeta,1} + K_{\zeta,2} \cdot X_{Re}^{K_{\zeta,3}} \right) \cdot K_{Ekin} \cdot \frac{(X_m)^2}{X_\rho},$$

$$X_{\Delta p} = \left[ K_{\zeta,1} + K_{\zeta,2} \cdot \left( K_{Re} \cdot \frac{X_m}{X_\eta} \right)^{K_{\zeta,3}} \right] \cdot X_{Ekin}, \text{ or}$$

$$X_{\Delta p} = \left[ K_{\zeta,1} + K_{\zeta,2} \cdot \left( K_{Re} \cdot \frac{X_m}{X_\eta} \right)^{K_{\zeta,3}} \right] \cdot K_{Ekin} \cdot \frac{(X_m)^2}{X_\rho}.$$

The aforementioned, defined flows with known Reynolds numbers, Re, known kinetic energy, $\rho U^2$, and known pressure curve required, in each case, for the measuring system parameters $K_{\zeta,1}$, $K_{\zeta,2}$, $K_{\zeta,3}$ or. $K_{Ekin}$ or $K_{Re}$, required for ascertaining the pressure difference, measured value, can be implemented sufficiently precisely directly on corresponding calibration facilities, for example, by means of calibration media known as regards flow characteristics, such as e.g. water, glycerin, etc., which are conveyed by means of correspondingly controlled pumps as impressed flow on the relevant measuring system to be calibrated. Alternatively thereto or in supplementation thereof, the flow parameters, such as the Reynolds number, the kinetic energy, the pressure difference, etc., required for ascertaining the measuring system parameters can, for example, also be ascertained metrologically by means of a pressure difference measuring system, which forms, together with the measuring system to be calibrated, one of the measuring systems proposed in the initially mentioned U.S. Pat. No. 7,406,878 and which, for the purpose of a wet calibration, is supplied with flows of correspondingly varied mass flow rates, densities and viscosities.

With application of the pressure difference, measured value $X_{\Delta p}$, it is then possible to correct correspondingly the phase difference between the primary signals $s_1$, $s_2$ influenced to a certain degree also by the pressure conditions in the flowing medium or also to correct the likewise influenced oscillation frequency, for the purpose of increasing the accuracy of measurement of mass flow- and/or density, measured value during operation. Additionally, it is, however, also possible, with application of the pressure difference, measured value $X_{\Delta p}$, to monitor the measuring system, or a pipeline system connected thereto, as regards states critical for the operation, for instance, the degree of a pressure drop in the flowing medium unavoidably caused by the measuring transducer and/or the therewith associated risk of, most often, damaging cavitation in the flowing medium as a result of a too high pressure reduction.

Therefore, according to an additional embodiment of the invention, the transmitter electronics is additionally designed to generate, with application of the pressure difference, measured value $X_{\Delta p}$, an alarm, which signals, visually and/or acoustically perceivably, an exceeding of an earlier defined, maximum allowable drop of static pressure in the medium flowing through the measuring transducer, or a too high pressure drop in the medium, for example, in the vicinity the measuring system, caused by the measuring transducer. The alarm can be brought about e.g. by the mentioned display- and operating element HMI on-site for display and/or by a horn controlled by means of the measuring system for hearing.

Alternatively thereto or in supplementation thereof, the transmitter electronics is, according to an additional embodiment of the invention, designed to generate, on the basis of the pressure difference, measured value as well as an internally held, first pressure, measured value $X_{p1}$, which represents a first pressure, $p_{Ref}$, reigning in the flowing medium, for example, one impressed by means of a pump providing the flowing medium and/or set by means of a valve and/or measured by means of an additional pressure sensor and/or ascertained by means of the transmitter electronics on the basis of at least one of the primary signals and/or a static, first pressure, $p_{Ref}$, a second pressure, measured value $X_{p2}$, with $X_{p2}=X_{p1}-X_{66\ p}$, which represents a static second pressure, $p_{crit}$, within the flowing medium, for example, thus a pressure at the site of the outlet-side reference point—here thus the second of the two reference points, which define the pressure difference represented by the pressure difference, measured value. For the mentioned case, in which one of the two reference points, by corresponding choice of the measuring system parameters for the pressure drop coefficients, or the pressure drop, characteristic curve, is placed at the earlier exactly ascertained site of minimum pressure $(\Delta p=\Delta p_{max})$ within the medium flowing in the measuring transducer, based on the second pressure, measured value $X_{p2}$, it can then be detected, for example, during operation of the measuring system, whether, within the measuring transducer or, in given cases, also directly in the outlet region of the connected pipeline lying downstream of the same, an unallowable low static pressure in the flowing medium is to be reckoned with. Therefore, the transmitter electronics of an additional embodiment is designed, with application of the second pressure, measured value $X_{p2}$, in given cases, to generate an alarm, which correspondingly signals, for instance, in a visually and/or acoustically perceivably manner, a subceeding, or falling beneath, of an earlier defined, minimum allowable static pressure in the medium and/or occurrence, e.g. an impending occurrence, of cavitation in the medium.

The first pressure, measured value $X_{p1}$ can be sent, for example, during operation, from the mentioned superordinated data processing system to the transmitter electronics and/or from a pressure sensor directly connected to the transmitter electronics, and thus, insofar, associated with the measuring system, to the transmitter electronics, and there stored in the mentioned volatile data memory RAM and/or in the non-volatile data memory EEPROM. Therefore, the measuring system, according to a further development, additionally comprises a pressure sensor communicating during operation with the transmitter electronics, for example, via a direct point-to-point connection and/or wirelessly per radio, for registering a static pressure reigning, for example, upstream of an inlet end of the measuring transducer or downstream of an outlet end of the measuring transducer, in a pipeline conveying the medium. Alternatively thereto or in supplementation thereof, the pressure, measured value $X_{p1}$, can, however, also, be ascertained, for example, with application of pressure measuring methods known to those skilled in the art, among other things, from the initially mentioned U.S. Pat. Nos. 6,868,740, 5,734,112, 5.576.500, US-A 2008/0034893 or WO-A 95/29386, WO-A 95/16897, by means of the transmitter electronics directly on the basis of the primary signals. For the case, in which the first pressure, measured value $X_{p1}$ represents not exactly that pressure in the medium, which corresponds to one of the two, reference points underpinning the pressure difference, measured value, for instance, because the pressure sensor delivering the pressure, measured value $X_{p1}$ or the controlled pump delivering the pressure, measured value $X_{p1}$ is farther removed from the inlet end of the measuring transducer, the pressure, measured value $X_{p1}$, is, of course, to be appropriately converted to the reference point, for instance, by corresponding subtraction or addition of a known pressure drop arising between the measuring point corresponding to the pressure, measured value $X_{p1}$ and the reference point defined by the calibration of the measuring system, or is to be correspondingly adjusted to the pressure drop, characteristic curve underpinning the above mentioned pressure drop-coefficient by selection of suitable measuring system parameters.

The measuring- and evaluating circuit of the measuring system of the invention serves, according to an additional embodiment of the invention, additionally to generate, derived in manner known, per se, to those skilled in the art from the oscillation frequency instantaneously represented by the frequency, measured value $X_f$, supplementally also the density, measured value $X_\rho$ required for ascertaining the pressure difference, measured value, for example, based on the relationship:

$$X_\rho = K_{\rho,1} + \frac{K_{\rho,2}}{X_f^2},$$

wherein $K_{p,1}$, $K_{p,2}$, are earlier experimentally ascertained measuring system parameters kept internally, for example, in the non-volatile data memory RAM, as constants correspondingly mediating between, on the one hand, the oscillation frequency represented by the frequency, measured value $X_f$ and, on the other hand, the density, $\rho$, to be measured.

Alternatively thereto or in supplementation thereof, the evaluating circuit, as quite usual in the case of In-line measuring devices of the type being discussed, in given cases, also can be used to ascertain the viscosity, measured value $X_\eta$, required for ascertaining the pressure difference, measured value; compare, for this, also the initially mentioned U.S. Pat. Nos. 7,284,449, 7,017,424, 6,910,366, 6,840,109, 5,576,500 or 6,651,513. For ascertaining the exciter energy or excitation power, or damping required for determining the viscosity, suitable, in such case, is, for example, the exciter signal delivered from the driver circuit of the transmitter electronics, especially an amplitude and frequency of its electrical current component driving the wanted mode or also an amplitude of the total, exciter current, in given cases, also normalized on an oscillation amplitude ascertained on the basis of at least one of the primary signals. Alternatively thereto or in supplementation thereof, however, also an internal control signal serving for tuning the driver signal, or the exciter current or, for example, in the case of an exciting of the vibrations of the at least one measuring tube with an exciter current of fixedly predetermined, or to constant controlled amplitude, also at least one of the primary signals, especially an amplitude thereof, can serve as a measure of the exciter energy or excitation power, or damping required for ascertaining the viscosity, measured value.

The aforementioned calculational functions, especially also those serving, in each case, for producing the pressure difference, measured value $X_{\Delta p}$, or others of the aforementioned measured values, can be implemented very simply e.g. by means of the above mentioned microcomputer of the evaluating circuit µC or, for example, also a digital signal processor DSP correspondingly provided therein. The creation and implementing of corresponding algorithms corresponding to the above-described formulas or, for example, also simulating the operation of the mentioned amplitude, or frequency control circuit for the exciter mechanism, as well as their translation into program-code correspondingly executable in the transmitter electronics, is known, per se, to those skilled in the art and needs, consequently, in any event, with knowledge of the present invention no detailed explanation. Of course, the aforementioned formulas, or other functionalities of the measuring system implemented with the transmitter electronics can also directly, wholly or partially, be implemented by means of corresponding discretely constructed and/or hybrid, thus mixed analog-digital, calculational circuits in the transmitter electronics TE.

While the invention has been illustrated and described in detail in the drawings and forgoing description, such illustration and description is to be considered as exemplary not restrictive in character, it being understood that only exemplary embodiments have been shown and described and that all changes and modifications that come within the spirit and scope of the invention as described herein are desired to protected.

What is claimed is:

1. A measuring system for flowing media, said measuring system comprising:
    a measuring transducer of a vibration-type, through which, during operation, a medium flows, and which produces primary signals corresponding with parameters of the flowing medium; as well as
    transmitter electronics electrically coupled with the measuring transducer for activating said measuring transducer and for evaluating primary signals delivered by said measuring transducer; wherein the measuring transducer includes:
    at least one measuring tube for conveying flowing medium, at least one electro-mechanical, oscillation exciter for exciting and/or maintaining vibrations of said at least one measuring tube;
    a first oscillation sensor for registering vibrations at least of said at least one measuring tube and for producing a first primary signal of said measuring transducer representing vibrations at least of said at least one measuring tube;
    and a second oscillation sensor for registering vibrations at least of said at least one measuring tube and for producing a second primary signal of said measuring transducer representing vibrations at least of said at least one measuring tube; and
    wherein said transmitter electronics:
    delivers at least one driver signal for said oscillation exciter effecting vibrations of said at least one measuring tube, and, generates, by means of the first primary signal and by means of the second primary signal as well as with application of a Reynolds number measured value ($X_{Re}$) representing a Reynolds number, Re, for medium flowing in said measuring transducer a pressure difference measured value ($X_{\Delta p}$), which represents a pressure difference occurring between two predetermined reference points in the flowing medium.

2. The measuring system as claimed in claim 1, wherein: each of the reference points is located within said measuring transducer.

3. The measuring system as claimed in claim 1, wherein: the Reynolds number measured value is held internally in a volatile data memory provided in said transmitter electronics and/or is produced during operation by means of the driver signal and/or by means of at least one of the primary signals.

4. The measuring system as claimed in claim 1, wherein: said transmitter electronics generates the Reynolds number measured value by means of the driver signal.

5. The measuring system as claimed in claim 1, wherein: said transmitter electronics generates the Reynolds number measured value by means of the first primary signal and/or by means of the second primary signal.

6. The measuring system as claimed in claim 1, wherein: said transmitter electronics generates the pressure difference measured value with application of an internally held viscosity measured value ($X_\eta$), which represents a viscosity, η, of medium flowing in said measuring transducer.

7. The measuring system as claimed in claim 6, wherein: said transmitter electronics generates the viscosity measured value by means of the driver signal.

8. The measuring system as claimed in claim 7, wherein: said transmitter electronics generates the viscosity measured value also with application of the first primary signal and/or the second primary signal.

9. The measuring system as claimed in claim 6, wherein: said transmitter electronics generates the Reynolds number measured value with application of the viscosity measured value ($X_\eta$).

10. The measuring system as claimed in claim 1, wherein: said transmitter electronics, for ascertaining the pressure difference measured value by means of the first primary signal and by means of the second primary signal, generates a phase difference measured value ($X_{\Delta\phi}$), which represents a phase difference, $\Delta\phi_1$, existing between the first primary signal and the second primary signal.

11. The measuring system as claimed in claim 1, wherein: said transmitter electronics, for ascertaining the pressure difference measured value on the basis of at least one of the primary signals and/or on the basis of the at least one driver signal, generates a frequency measured value ($X_f$), which represents an oscillation frequency, $f_{exc}$, of vibrations of said at least one measuring tube.

12. The measuring system as claimed in claim 1, wherein: said transmitter electronics, for ascertaining the pressure difference measured value ($X_{\Delta p}$) by means of the first primary signal and by means of the second primary signal, generates a mass flow measured value ($X_m$), which represents a mass flow rate, of medium flowing in the measuring transducer.

13. The measuring system as claimed in claim 12, wherein: the transmitter electronics, for ascertaining the pressure difference measured value on the basis of at least one of the primary signals and/or on the basis of the at least one driver signal, generates a phase difference measured value ($X_{\Delta\phi}$), which represents a phase difference, A(P1, existing between the first primary signal and the second primary signal, as well as a frequency measured value ($X_f$), which represents an oscillation frequency, $f_{exc}$, of vibrations of the at least one measuring tube, and the transmitter electronics generates the mass flow measured value ($X_m$) based on the relationship:

$$X_m = K_m \cdot \frac{X_{\Delta \varphi}}{X_f}$$

wherein $K_m$ is an earlier experimentally ascertained, measuring system parameter.

14. The measuring system as claimed in claim 1, wherein: said transmitter electronics generates the pressure difference measured value ($X_{\Delta p}$) with application of a density measured value ($X_\rho$) representing a density, $\rho$, of medium flowing in the measuring transducer.

15. The measuring system as claimed in claim 11, wherein: said transmitter electronics generates the density measured value ($X_\rho$) by means of the frequency measured value ($X_f$).

16. The measuring system as claimed in claim 1, wherein: said transmitter electronics, for ascertaining the pressure difference measured value ($X_{\Delta p}$) by means of the first primary signal and by means of the second primary signal, generates a flow energy measured value ($X_{Ekin}$), which represents a kinetic energy, $\rho U^2$, of medium flowing in said measuring transducer, dependent on a density, $\rho$, and a flow velocity, U, of medium flowing in said measuring transducer.

17. The measuring system as claimed in claim 16, wherein: said transmitter electronics generates the flow energy, measured value ($X_{Ekin}$) based on the relationship:

$$X_{Ekin} = K_{Ekin} \cdot \frac{(X_m)^2}{X_\rho},$$

wherein $K_{Ekin}$ is an earlier experimentally ascertained measuring system parameter.

18. The measuring system as claimed in claim 12, wherein: said transmitter electronics generates the pressure difference measured value ($X_{\Delta p}$) based on the relationship:

$$X_{\Delta p} = \left( K_{\zeta,1} + K_{\zeta,2} \cdot X_{Re}^{K_{\zeta,3}} \right) \cdot K_{Ekin} \cdot \frac{(X_m)^2}{X_\rho},$$

wherein $K_{\zeta,1}$, $K_{\zeta,2}$, $K_{\zeta,3}$, $K_{Ekin}$ are earlier experimentally ascertained measuring system parameters.

19. The measuring system as claimed in claim 12, wherein: said transmitter electronics generates the Reynolds number measured value ($X_{Re}$) with application both of the mass flowmeasured value ($X_m$) as well as also the viscosity measured value ($X_\eta$).

20. The measuring system as claimed in claim 1, wherein: said transmitter electronics, for ascertaining the pressure difference measured value ($X_{\Delta p}$), generates a pressure drop coefficient ($X_\zeta$), which represents a pressure drop across said measuring transducer, dependent on the instantaneous Reynolds number, Re, of the flowing medium, referenced to an instantaneous kinetic energy of the medium flowing in said measuring transducer.

21. The measuring system as claimed in claim 20, wherein: said transmitter electronics generates the pressure difference measured value ($X_{\Delta p}$) with application of the pressure drop coefficients ($X_\zeta$).

22. The measuring system as claimed in claim 1, wherein: said transmitter electronics, with application of the pressure difference measured value ($X_{\Delta p}$) and on the basis of a first pressure measured value ($X_{p1}$), which represents a first pressure, $p_{Ref}$, reigning in the flowing medium, generates a second pressure measured value ($X_{p2}$), which represents a static second pressure, $p_{crit}$, within the flowing medium.

23. The measuring system as claimed in claim 22, wherein: said transmitter electronics, with application of the second pressure measured value ($X_{p2}$), generates an alarm, which signals a subceeding, or falling beneath, of an earlier defined, minimum allowable static pressure in the medium; and/or
wherein said transmitter electronics, with application of the second pressure, measured value ($X_{p2}$), generates an alarm, which signals an occurrence of cavitation in the medium.

24. The measuring system as claimed in claim 1, which, for producing a pressure measured value ($X_{p1}$) representing a static pressure reigning in the flowing medium, further comprises:
a pressure sensor serving for registering a static pressure reigning in a pipeline conveying the medium and for communicating, during operation, with said transmitter electronics.

25. The measuring system as claimed in claim 1, wherein: said transmitter electronics, with application of the pressure difference measured value, generates an alarm, which signals an exceeding of an earlier defined, maximum allowable drop of a static pressure in the medium flowing through the measuring transducer; and/or
wherein said transmitter electronics, with application of the pressure difference measured value, generates an alarm, which signals a too high pressure drop caused by the measuring transducer in the medium.

26. The measuring system as claimed in claim 1, wherein, the measuring transducer further comprises:
a measuring transducer housing with an inlet-side, first housing end, and with an outlet-side, second housing end.

27. The measuring system as claimed in claim 26, wherein: the inlet-side, first housing end of said measuring transducer housing is formed by means of an inlet-side, first flow divider including two, mutually spaced flow openings and the outlet-side, second housing end of the measuring transducer housing is formed by means of an outlet-side, second flow divider including two, mutually spaced flow openings; and
wherein said measuring transducer includes two, mutually parallel, measuring tubes for conveying flowing medium, of which measuring tubes a first measuring tube opens with an inlet-side, first measuring tube end into a first flow opening of the first flow divider and with an outlet-side, second measuring tube end into a first flow opening of the second flow divider, and a second measuring tube opens with an inlet-side, first measuring tube end into a second flow opening of the first flow divider and with an outlet-side, second measuring tube end into a second flow opening of the second flow divider.

28. The measuring system as claimed in claim 27, wherein: said at least one electro-mechanical, oscillation exciter serves for exciting and/or maintaining opposite equal vibrations of said first measuring tube and said second measuring tube.

29. The measuring system as claimed in claim 28, wherein:
the first primary signal, produced by means of said first oscillation sensor, represents inlet-side vibrations, which make the first and second measuring tubes relative to each other; and
second primary signal, produced by means of said second oscillation sensor, represents outlet-side vibrations, which make the first and second measuring tubes relative to each other.

30. The measuring system as claimed in claim 26, wherein:
the pressure difference measured value represents a pressure difference occurring in the flowing medium from said first housing end to said second housing end.

31. A method for measuring a pressure difference arising within a flowing medium, said method comprising the steps of:
permitting the medium to flow through at least one measuring tube;
exciting the at least one measuring tube to vibrations;
producing a first primary signal representing inlet-side vibrations at least of the at least one measuring tube as well as a second primary signal representing outlet-side vibrations at least of the at least one measuring tube;
applying the first primary signal and/or the second primary signal for producing a Reynolds number measured value representing a Reynolds number, Re, for the flowing medium;
and applying the Reynolds number measured value for producing a pressure difference measured value, which represents a pressure difference occurring between two reference points in the flowing medium.

32. The method as claimed in the claim 31, further comprising the step of:
exciting bending oscillations about an imaginary oscillation axis imaginarily connecting an inlet-side, first measuring tube end of the measuring tube and an outlet-side, second measuring tube end of the measuring tube for producing said first and second primary signals.

33. The method as claimed in claim 32, further comprising at least one of:
applying the first primary signal and/or the second primary signal for producing a density measured value representing a density of the flowing medium and/or for producing a mass flow measured value representing a mass flow rate of the flowing medium.

34. The method as claimed in claim 32, further comprising the steps of:
producing a mass flow measured value representing a mass flow rate of the flowing medium by means of the first primary signal and by means of the second primary signal;
producing a density-measured value representing a density of the flowing medium; and
applying the mass flow measured value, the density measured value as well as the Reynolds number measured value for the producing the pressure difference measured value.

35. A measuring system as claimed in claim 22, wherein:
the first pressure measured value ($X_{p1}$) is held internally in a volatile data memory provided in the transmitter electronics.

36. The measuring system as claimed in claim 22, wherein the first pressure measured value ($X_{p1}$) represents a first pressure, $P_{Ref}$, upstream of an outlet end of the measuring transducer and/or downstream of an inlet end of the measuring transducer; and/or
wherein the second pressure, measured value ($X_{p2}$) represents a static second pressure, $p_{crit}$, a minimum static second pressure and/or a static second pressure classified as critical for the measuring system.

37. The measuring system as claimed in claim 22, wherein:
the first pressure, $P_{Ref}$, is measured by means of a pressure sensor communicating with the transmitter electronics.

38. The measuring system as claimed in claim 1, wherein:
said transmitter electronics, with application of the pressure difference measured value ($X_{\Delta p}$) and on the basis of a first pressure measured value ($X_{p1}$) which represents a first pressure, $p_{Ref}$, reigning in the flowing medium upstream of an outlet end of the measuring transducer and/or downstream of an inlet end of the measuring transducer, generates a second pressure measured value (Xp2), which represents a static second pressure, $P_{crit}$, within the flowing medium.

39. The measuring system as claimed in claim 1, wherein:
said transmitter electronics, with application of the pressure difference measured value ($X_{\Delta p}$) and on the basis of a first pressure measured value ($X_{p1}$), which represents a first pressure, $p_{Ref}$, reigning in the flowing medium, generates a second pressure measured value ($X_{p2}$), which represents a static second pressure, $p_{crit}$, within the flowing medium, said static second pressure, $p_{crit}$, is a minimum static second pressure and/or classified as critical for the measuring system.

40. The measuring system as claimed in claim 2, wherein:
each of the reference points is located within the measuring transducer in such a manner, that a first of the two reference points is located on the inlet side and a second of the two reference points is located on the outlet side in the measuring transducer.

41. The measuring system as claimed in claim 6, wherein the viscosity measured value ($X_{72}$) is held in a volatile data memory; and/or
wherein the viscosity measured value ($X_{72}$) is produced during operation by means of the driver signal and/or by means of at least one of the primary signals.

42. The measuring system as claimed in claim 11, wherein:
the frequency measured value ($X_f$) represents an oscillation frequency, $f_{exc}$, of bending oscillations of the at least one measuring tube executed about an imaginary oscillation axis imaginarily connecting an inlet-side, first measuring tube end of the measuring tube and an outlet-side, second measuring tube end of the measuring tube at a natural resonance frequency of the measuring transducer.

43. The measuring system as claimed in claim 14, wherein the density measured value ($X_\rho$) is held in a volatile data memory; and/or
wherein the density measured value ($X_\rho$) is produced during operation by means of the driver signal and/or by means of at least one of the primary signals.

44. The measuring system as claimed in claim 19, wherein:
said transmitter electronics generates the Reynolds number measured value ($X_{Re}$) based on the relationship:

$$X_{Re} = K_{Re} \cdot \frac{X_m}{X_\eta},$$

wherein $K_{Re}$ is an measuring system parameter ascertained in a calibration of the measuring system and/or by means of computer based calculations and/or held as a constant internally in a non-volatile data memory provided in the transmitter electronics.

45. The measuring system as claimed in claim 20, wherein:
said transmitter electronics generates the pressure drop coefficient ($X_\zeta$) based on the relationship:

$$X_\zeta = K_{\zeta,1} + K_{\zeta,2} \cdot X_{Re}^{K_{\zeta,3}},$$

wherein $K_{\zeta,1}$, $K_{\zeta,2}$, $K_{\zeta,3}$, are earlier experimentally ascertained, measuring system parameters held internally as constants in a non-volatile data memory provided in the transmitter electronics.

46. The measuring system as claimed in claim 21, wherein:
said transmitter electronics generates the pressure difference measured value ($X_{\Delta p}$) based on the relationship:

$$X_{\Delta p} = X_\zeta \cdot K_{Ekin} \cdot \frac{(X_m)^2}{X_\rho}$$

wherein $K_{Ekin}$ is an earlier ascertained, measuring system parameter held as a constant internally in a non-volatile data memory provided in the transmitter electronics.

47. The measuring system as claimed in claim 26, wherein:
the pressure difference measured value represents a difference occurring in the flowing medium from the first housing end to the second housing end, with the first reference point for the pressure difference represented by the pressure difference measured value is located in the inlet-side, first housing end of the measuring transducer housing and the second reference point for the pressure difference represented by the pressure difference, measured value is located in the outlet-side, second housing end of the measuring transducer housing.

48. The measuring system as claimed in claim 14, wherein:
said transmitter electronics generates the pressure difference measured value ($X_{\Delta p}$) based on the relationship:

$$X_{\Delta p} = \left(K_{\zeta,1} + K_{\zeta,2} \cdot X_{Re}^{K_{\zeta,3}}\right) \cdot K_{Ekin} \cdot \frac{(X_m)^2}{X_\rho},$$

wherein $K_{\zeta,1}$, $K_{\zeta,2}$, $K_{\zeta,3}$, $K_{Ekin}$ are earlier experimentally ascertained measuring system parameters.

* * * * *